(12) United States Patent
Keall et al.

(10) Patent No.: US 7,835,493 B2
(45) Date of Patent: Nov. 16, 2010

(54) METHOD AND SYSTEM FOR FOUR DIMENSIONAL INTENSITY MODULATED RADIATION THERAPY FOR MOTION COMPENSATED TREATMENTS

(75) Inventors: Paul J. Keall, Stanford, CA (US); Yelin Suh, Palo Alto, CA (US); Elisabeth Weiss, Williamsburg, VA (US)

(73) Assignee: Stanford University, Palo Alto, CA (US)

( * ) Notice: Subject to any disclaimer, the term of this patent is extended or adjusted under 35 U.S.C. 154(b) by 46 days.

(21) Appl. No.: 12/187,222

(22) Filed: Aug. 6, 2008

(65) Prior Publication Data

US 2009/0041188 A1 Feb. 12, 2009

Related U.S. Application Data

(60) Provisional application No. 60/954,206, filed on Aug. 6, 2007.

(51) Int. Cl.
*A61N 5/10* (2006.01)
*H05G 1/08* (2006.01)

(52) U.S. Cl. .......................... 378/65; 378/95
(58) Field of Classification Search ................ 378/65, 378/95

See application file for complete search history.

(56) References Cited

U.S. PATENT DOCUMENTS 7,221,733 B1 * 5/2007 Takai et al. ............... 378/65
7,609,810 B2 * 10/2009 Yi et al. .................... 378/65
2008/0049897 A1 * 2/2008 Molloy ..................... 378/65
2008/0081991 A1 * 4/2008 West et al. ................ 600/425
2008/0253636 A1 * 10/2008 Deller ....................... 382/131

OTHER PUBLICATIONS

Paul Keall, "4-D CT Imaging and Treatment Planning", Seminars in Radiation Oncology, vol. 14, No. 1 Jan. 2004: pp. 81-90.*
Rietzel E. et al., "Four-Dimensional image-based treatment planning: target volume segmentation and dose calculation in the presence of respiratory motion", International Journal of Radiation: Oncology Biology Physics, Pergamon Press, US vol. 61, No. 5, Apr. 1, 2005, pp. 1535-1550, XP004842268, ISSN: 0360-3016.*

\* cited by examiner

*Primary Examiner*—Edward J Glick
*Assistant Examiner*—Thomas R Artman
(74) *Attorney, Agent, or Firm*—Whitham, Curtis, Christofferson & Cook, P.C.

(57) ABSTRACT

A deliverable four dimensional (4D) intensity modulated radiation therapy (IMRT) planning method is disclosed, for delivery using a linear accelerator with a dynamic multi-leaf collimator (DMLC). A 4D computed tomography (CT) scan is used for segmenting tumor anatomy on a reference phase of periodic motion of the tumor. Deformable registration of the 4D CT data is used to generate corresponding anatomical structures on other phases. Preferably, the collimator for each beam position is aligned using the gross tumor volume (GTV) centroid motion corresponding to the periodic motion of the tumor, as determined from the two dimensional (2D) projection of a given beam position. A deliverable IMRT plan is created on the 4D CT image set in which the MLC leaf positions and beam on/off status can vary as a function of respiratory phase by solving a four dimensional optimization problem. The mechanical constraints of the MLC leaves are included in the optimization.

4 Claims, 20 Drawing Sheets

Formalism for deliverable 4D IMRT planning method

4D optimal

Find deliverable fluence, $\Psi(\theta)$, to satisfy $\min\left\{f\left[D_{Rx}(\Psi(\theta))\right]\right\}$ where $f$ is a mathematical cost function representation of a clinical objective, and $$D_{Rx} = \sum_{\text{Phase } \phi=1}^{P} \lambda_{\phi}^{\theta} D_{Rx}^{\phi}\left(I(x + u(x,\theta)) | \Psi(\theta)\right).$$

Current approach

Find deliverable fluence, $\Psi_{\phi_0}$, to satisfy $\min\left\{f\left[D_{Rx}(\Psi_{\phi_0})\right]\right\}$ where $D_{Rx} = D_{Rx}\left(I(x)_{\phi_0} | \Psi_{\phi_0}\right)$ and $\theta_0$ is the exhale phase. For other phases, $\Psi(\theta) = \Psi_{\phi_0} + g(\theta)$ where $g(\theta)$ is the PTV centroid displacement from phase $0 \to \theta$ along the major axis of motion in the beam view (collimator aligned with major axis of motion from 4D CT).

Comparison method

Find deliverable fluence, $\Psi_\theta$, to satisfy $\min\left\{f\left[D_{Rx}(\Psi_\theta)\right]\right\}$ for each phase, i.e. ignore leaf motion constraints.

Figure 1

Lung cancer patient details

| Patient # | GTV volume (cm³) | GTV centroid motion range (cm) |
|---|---|---|
| 1 | 3.0 | 2.1 |
| 2 | 61.0 | 0.4 |
| 3 | 12.5 | 0.5 |
| 4 | 1.0 | 0.6 |
| 5 | 20.4 | 0.1 |
| 6 | 5.2 | 0.4 |
| 7 | 323.6 | 0.2 |
| 8 | 23.0 | 0.3 |
| 9 | 6.1 | 0.2 |
| 10 | 7.5 | 0.5 |
| 11 | 119.2 | 1.3 |
| 12 | 7.5 | 1.1 |
| mean (min, max) | 49.2 (1.0, 323.6) | 0.6 (0.1, 2.1) |

Figure 4

METHOD AND SYSTEM FOR FOUR DIMENSIONAL INTENSITY MODULATED RADIATION THERAPY FOR MOTION COMPENSATED TREATMENTS

This application claims the benefit of U.S. Provisional Application No. 60/954,206 titled "METHOD FOR FOUR DIMENSIONAL INTENSITY MODULATED RADIATION THERAPY FOR MOTION COMPENSATED TREATMENTS" filed on Aug. 6, 2007.

FEDERALLY-SPONSORED RESEARCH OR DEVELOPMENT

This invention was made with Government support under contract CA093626 awarded by the National Institutes of Health. The Government has certain rights in this invention.

BACKGROUND OF THE INVENTION

1. Field of the Invention

The present invention generally relates to oncological radiation therapy and more particularly to use of motion compensated treatment plans.

2. Background Description

Radiation therapy for cancerous tumors may involve adverse side effects because of the difficulty of confining the radiation to the target tumor. Side effects may range from temporary damage to healthy tissues that regenerate following treatment to irreversible damage to healthy tissues that cannot regenerate. Side effects of radiation can be minimized by planning and delivery of a course of radiotherapy. For example, where treatment technology involves irradiation of healthy tissue in addition to the tumor, a treatment plan may use a succession of doses that allows time between successive doses for damaged tissues to regenerate, and where each dose is small enough to avoid damage to tissues that cannot regenerate. Typically, a treating physician will use a dose volume histogram (DVH) to prescribe radiation therapy and a radiation technician will apply a delivery technology so as to conform to the prescribed DVH as closely as possible. Various techniques have been developed to enable a prescribed DVH to be followed more closely and with reduced side effects.

One such technique is conformal radiotherapy (CRT), which has been in use since 1960. This uses a single radiation beam, with special blocks or collimators to more tightly control the treatment field. Since the late 1990's a more versatile approach to conformal radiotherapy has been in use. This approach uses radiation beams made up of hundreds of small components, allowing the treatment field to follow curves and contours of the tumor. This approach is called Intensity Modulated Radiation Therapy (IMRT), and typically requires very detailed treatment planning along with computer analysis.

Another group of techniques has been developed to compensate for motion of tumors in the patient during treatment (e.g. where doses of radiation must be administered to a thoracic tumor which moves as the patient breathes). Four Dimensional Computed Tomography (4D CT) scanning techniques are used to adjust the delivered radiation field to compensate for tumor motion over the breathing cycle.

Commercial algorithms exist for intensity modulated radiotherapy delivery, and for using four dimensional computed tomography scans. However, no feasible treatment planning algorithm exists for using IMRT on 4D CT scans, with the intensity modulated radiation field being provided by a linear accelerator (linac) and a dynamic multi-leaf collimator (DMLC).

SUMMARY OF THE INVENTION

It is therefore an object of the present invention to provide a feasible algorithm for IMRT treatment planning based on four-dimensional CT scans for treatment delivery, with the intensity modulated radiation field being provided by a linac with a DMLC.

A further object of the invention is to provide a plan suitable for continuous beam-target alignment during radiation treatment delivery.

It is also an object of the invention to provide a treatment planning algorithm that accounts explicitly for deformation, including multiple targets with different motion, during treatment optimization, whilst still including treatment delivery constraints.

The finite mechanical motion capabilities of a multi-leaf collimator (MLC) impose constraints on 4D IMRT planning for DMLC tumor tracking. These motion constraints need to be incorporated to create plans for linac radiotherapy where the MLC-defined treatment beam follows the tumor motion using real-time feedback. Further, the irregularities of target motion are to be noted. While DMLC tumor tracking is able to rely upon motion (e.g. from the breathing cycle) that has important periodic properties, there is variation over time in the length of a cycle and in the timing during the cycle of the relative position of the tumor along the track of the more or less cyclic motion. The track of motion has some variability from cycle to cycle, the duration of the cycle also varies, and the timing of tumor motion along the track is not precisely predictable. For these reasons the term "irregular periodic motion" will be used to describe tumor motion in the context of DMLC tumor tracking.

The deliverable 4D IMRT planning method of the Specific Embodiment of the invention involves three essential steps: (1) The collimator angle for each beam is aligned to the major axis of the gross tumor volume (GTV) centroid motion for the respiratory phases, as determined from the two dimensional (2D) projection of a given beam. (2) An IMRT plan is created on the exhale phase of the 4D CT image set creating MLC leaf positions for each beam. (3) IMRT plans at other respiratory phases are generated by translating the exhale phase MLC leaf positions by the relative displacement of the GTV centroid for each phase, keeping the collimator angle for each beam the same.

An aspect of the invention is a method for four-dimensional (4D) intensity modulated radiation therapy (IMRT) planning for motion compensated treatments. The method comprises creating a deliverable IMRT treatment plan for a tumor in irregular periodic motion, the irregular period of motion comprising a plurality of phases, the treatment plan comprising treatment plans for each of the plurality of phases, each treatment plan being delivered using a multi-leaf collimator whose leaf positions are adapted separately for each respective phase and for each of a plurality of beam positions, the beam being collimated by said multi-leaf collimator.

In another aspect the method of the invention further comprises determining a gross tumor volume (GTV) centroid for each of the phases, designating one of the phases as a reference phase, and targeting the collimator for each phase by a displacement relative to the GTV centroid of the reference phase.

A further aspect of the invention is to define phases by dividing the irregular period of motion into parts, measured by time or by tumor position. For example, phases could be defined by dividing the irregular period into equal parts of time. Then, the adapted leaf positions may be held constant during each phase.

It is also an aspect of the method of the invention to import a 4D computed tomography (CT) scan for the tumor, the 4D CT scan comprising a CT scan for each of the plurality of phases, manually segmenting anatomy on the reference phase CT scan, and using deformable registration to automatically generate corresponding anatomical structures for each phase, based upon the manual segmentation of the reference phase and a corresponding 4D CT scan of each phase.

It is a further aspect of the invention to provide treatment planning for 4D anatomy allowing MLC leaves to vary as a function of dose delivered (monitor units) and respiratory phase (time), while also allowing for beam on/off at different respiratory phases.

The present invention was devised during a study to develop a deliverable 4D IMRT planning method for DMLC tumor tracking delivery, where the method was compared to an unconstrained 4D IMRT planning method.

BRIEF DESCRIPTION OF THE DRAWINGS

The foregoing and other objects, aspects and advantages will be better understood from the following detailed description of a preferred embodiment of the invention with reference to the drawings, in which:

FIG. 1 shows the mathematical formalism for a deliverable 4D IMRT planning method using the invention.

FIG. 4 is a table showing gross tumor volume and GTV centroid motion range for the twelve patients whose data were used to evaluate the invention.

DETAILED DESCRIPTION OF A PREFERRED EMBODIMENT OF THE INVENTION

Figure 2A:
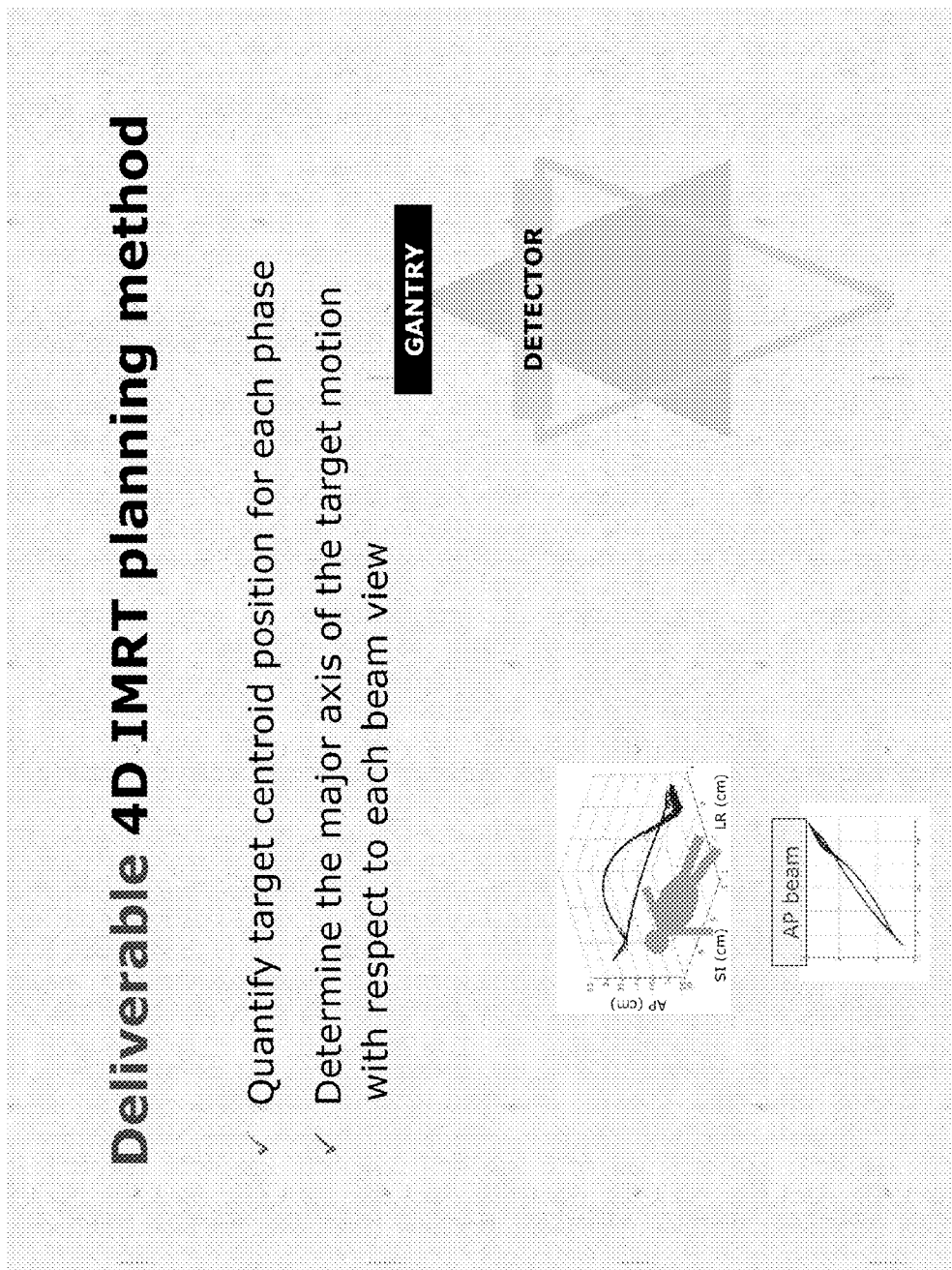
FIGS. 2A and 2B show major axis determination from 2D projection of given beams (anteroposterior or AP beam in FIG. 2A, and lateral beam in FIG. 2B). Once major axis is determined for a given beam, the collimator is rotated to align MLC motion parallel to major axis for each beam (FIG. 2C).
Figure 2B:
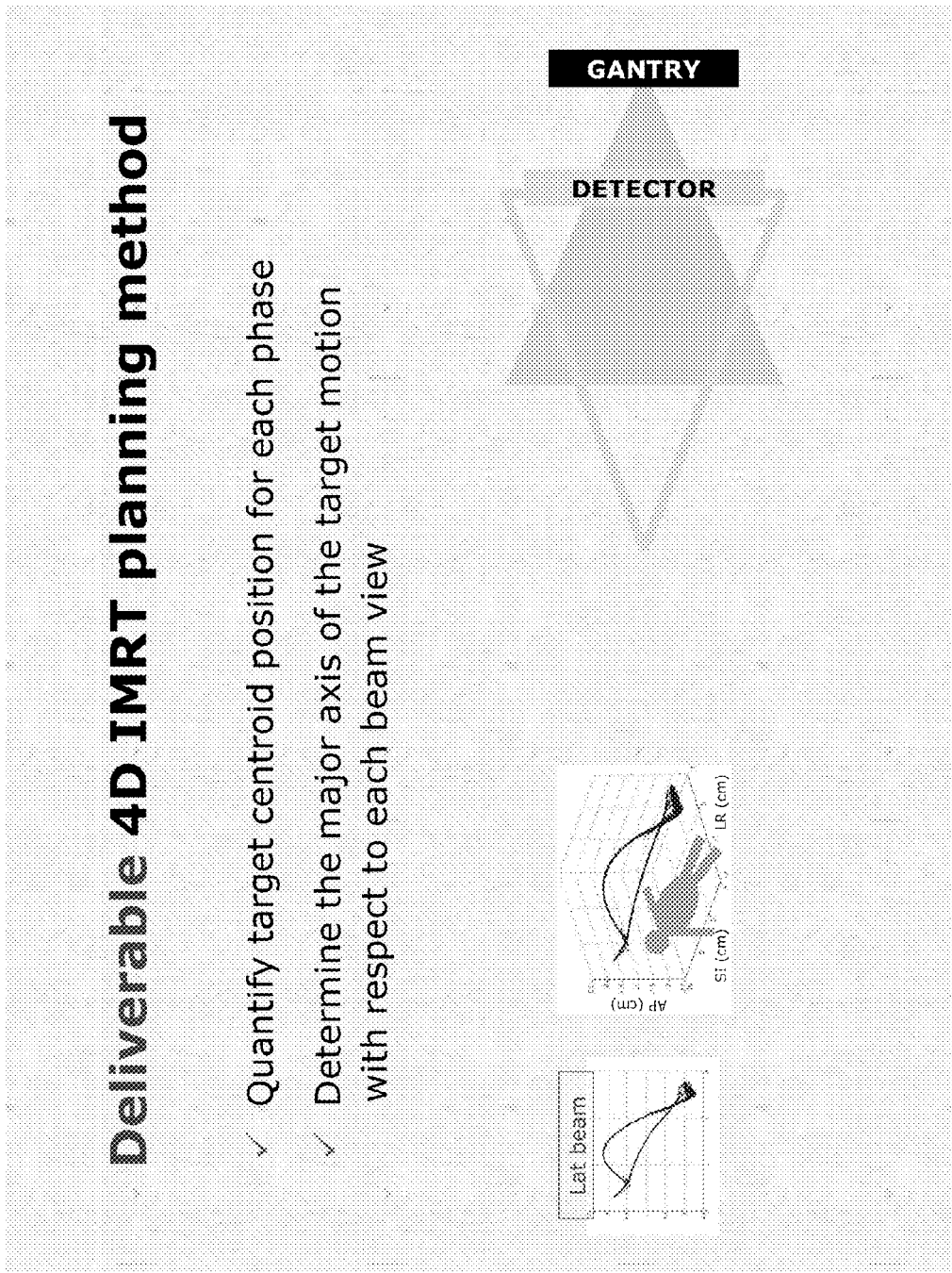
Figure 2C:
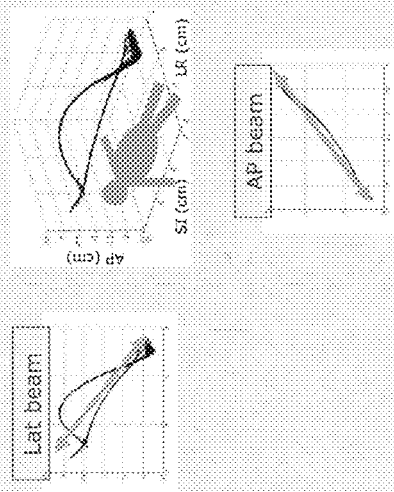

Referring now to the drawings, and more particularly to FIG. 1, there is shown a formalism for evaluating a deliverable 4D IMRT planning method according to the invention. For a given clinical presentation, an optimal deliverable fluence $\Psi(\theta)$ is found and used to find a current deliverable fluence for the exhale phase. A current deliverable fluence for the other phases is found using the GTV centroid displacement from the exhale phase, based upon 4D CT data where the collimator is aligned with the major axis of motion and leaf motion constraints are ignored. This is done with respect to each beam view, as illustrated in FIGS. 2A, 2B and 2C.

Figure 3:
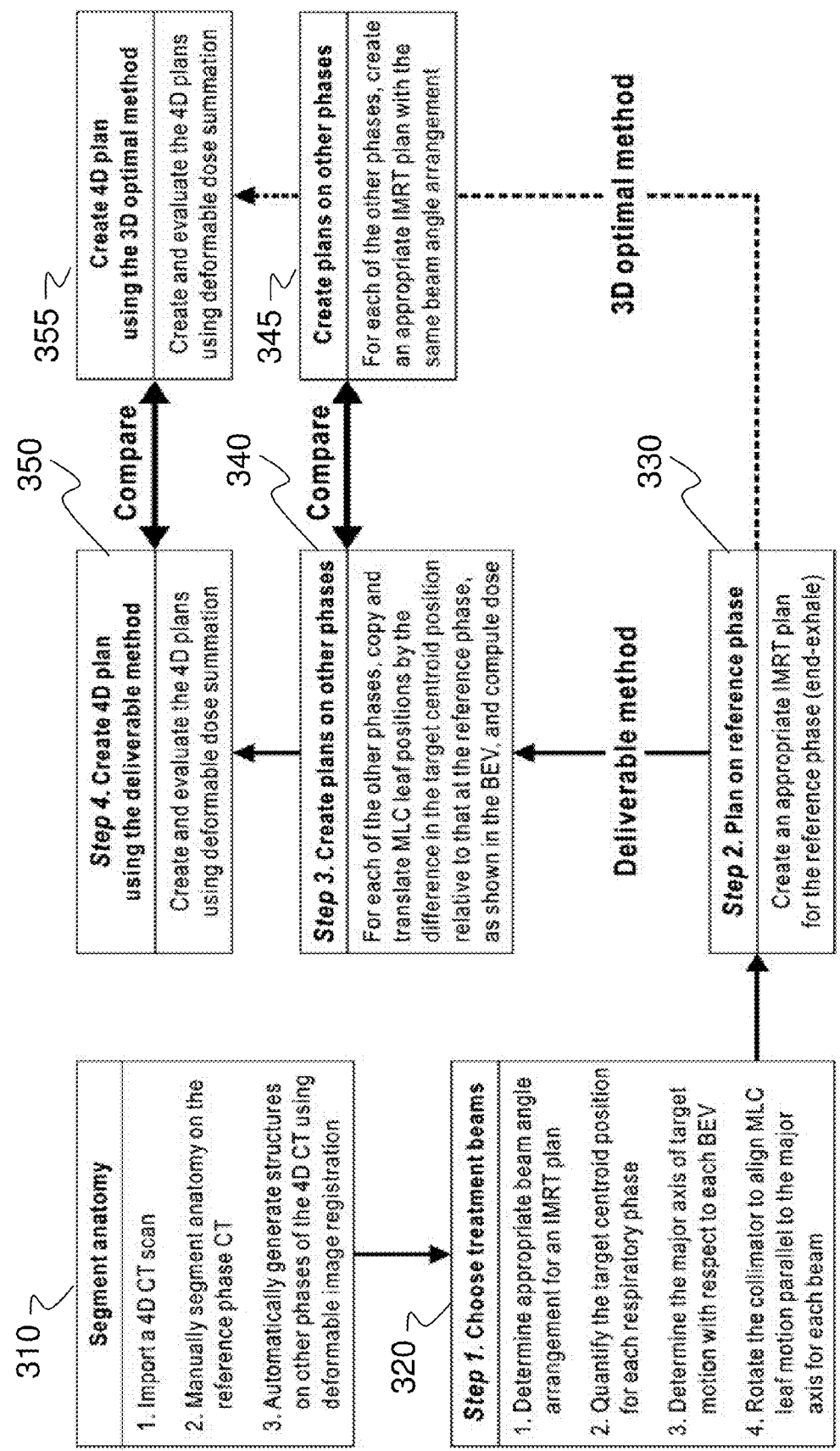
FIG. 3 is a flowchart showing the steps for a deliverable 4D IMRT planning method.

A flow chart of the method is detailed in FIG. 3. In an anatomic segmentation step 310 a 4D CT scan is imported, the anatomy on the reference phase CT is manually segmented, structures on other phases are automatically generated using deformable registration. The collimator is then aligned 320 by determining the appropriate beam angle arrangement for an IMRT plan, quantifying a target centroid position for each respiratory phase, determining the major axis of the target motion with respect to each beam view, and rotating the collimator to align MLC motion parallel to the major axis for each beam. An appropriate IMRT plan is then created 330 on a reference phase (e.g. end of exhale).

IMRT plans are then created on each of the other phases 340 by copying and translating the MLC leaf position by the difference in the target centroid position relative to that at the reference phase, as projected in the beam view, and then importing MLC files and computing dose. These plans may be compared to plans created with the same beam angle arrangement without the constraints consequent upon translation of MLC leaf positions, under optimal 3D assumptions 345. Finally, a composite plan is created and evaluated 350 using deformable dose summation. This composite plan may be compared to an unconstrained 4D plan 355 created from deformable dose summations from 3D optimal plans for each phase.

To test the deliverable 4D IMRT planning method, 4D CT image sets from twelve lung cancer patients were used. A table showing GTV volume and GTV centroid motion range for these twelve patients is provided in FIG. 4. The mean of the patient GTV volumes and range of GTV motion were 49 cm³ (1-324 cm³) and 0.6 cm (0.1-2.1 cm), respectively. Contours were automatically generated using deformable image registration on each phase of each 4D CT scan based on the contours manually segmented on the inhale phase for each patient. The deliverable plans were compared with unconstrained plans. The unconstrained plans were optimized for each respiratory phase of the 4D CT image sets, thus accounting for deformation and hysteresis but ignoring leaf motion constraints. The deliverable and unconstrained plans were compared using a one-tailed student's t-test with the null hypothesis of $H_0: X_{unc} = X_{del}$ and the alternative hypothesis of $H_A: X_{unc} > X_{del}$, where X is a dose-volume evaluation metric derived from the dose-volume histogram from the plan for each phase for each patient.

Results and Discussion:

Table A shows the mean and standard deviation of dose-volume metric ratios, $$\overline{X_{unc}^{del}} = \frac{\sum_{j}^{N}\sum_{i}^{M} X_{del}^{i,j}/X_{unc}^{i,j}}{N \cdot M} \text{ and}$$

$$\sigma_{\overline{X_{unc}^{del}}} = \sqrt{\frac{\sum_{j}^{N}\sum_{i}^{M}\left(X_{del}^{i,j}/\overline{X_{unc}^{i,j}} - \overline{X_{unc}^{del}}\right)^2}{N \cdot M}},$$

respectively, where j is the patient number and k is the phase number. All mean values of the dose and volume metric ratios were very close to 1, which means the deliverable and unconstrained plans had similar dose-volume characteristics. No evaluated dose-volume metric was statistically different between the deliverable and unconstrained methods. The relatively small differences between the deliverable and unconstrained methods is highlighted in the graphs and corresponding cross-sectional dosage contour comparisons shown for the best, least and worst score ratio agreements shown in FIGS. 6A-8B.

Figure 5:
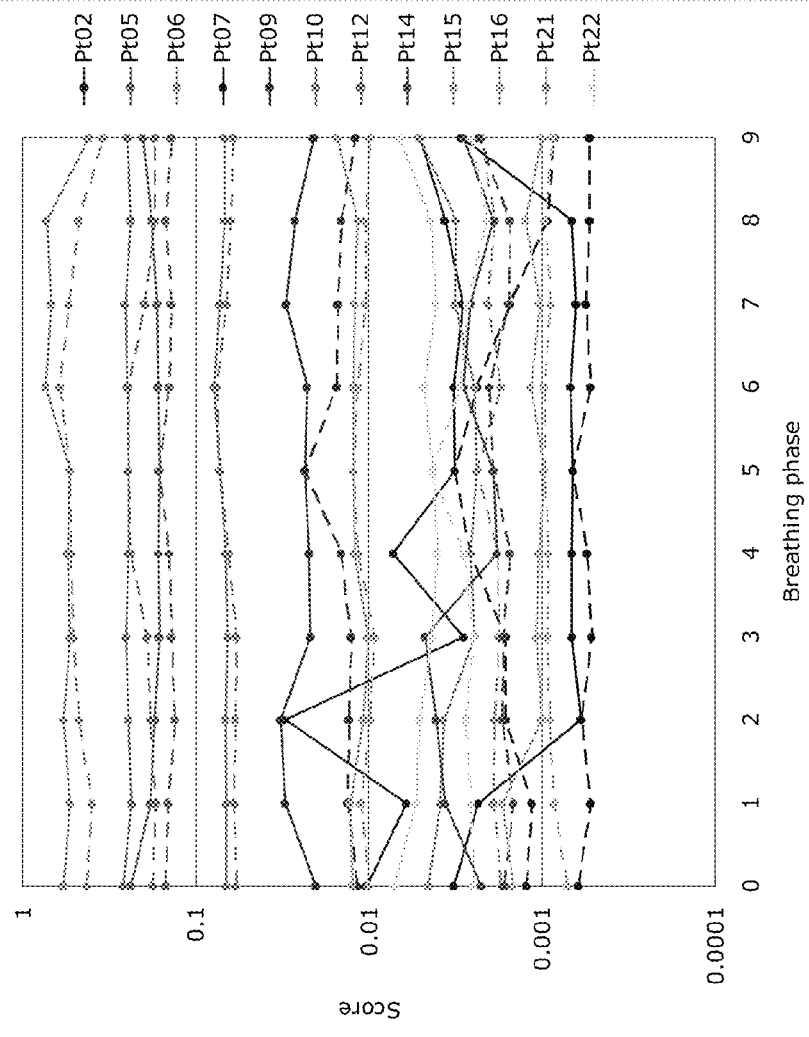
FIG. 5 is a composite graph showing comparative scores for each the twelve patients for each of nine breathing phases for the deliverable method of the invention evaluated against the benchmark unconstrained method.
Figure 6A:
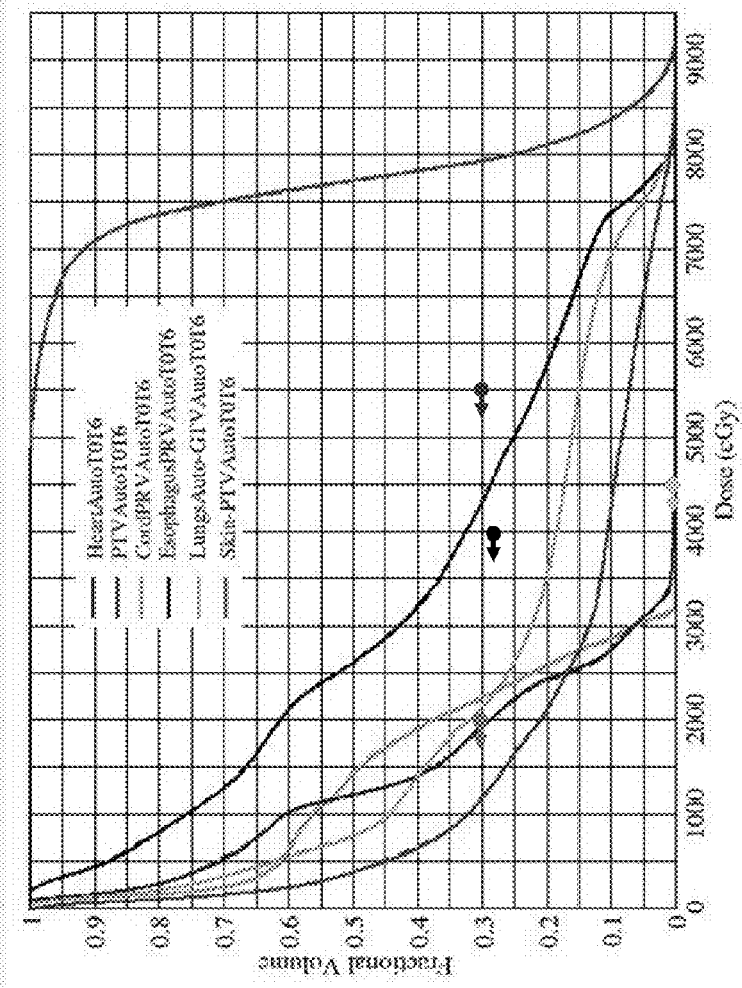
FIG. 6A shows DVH from the best agreement case, whose score ratio was 1.01, where the two sets of DVH are on top of each other indicating that plans from the deliverable and unconstrained methods are almost the same.
Figure 6B:
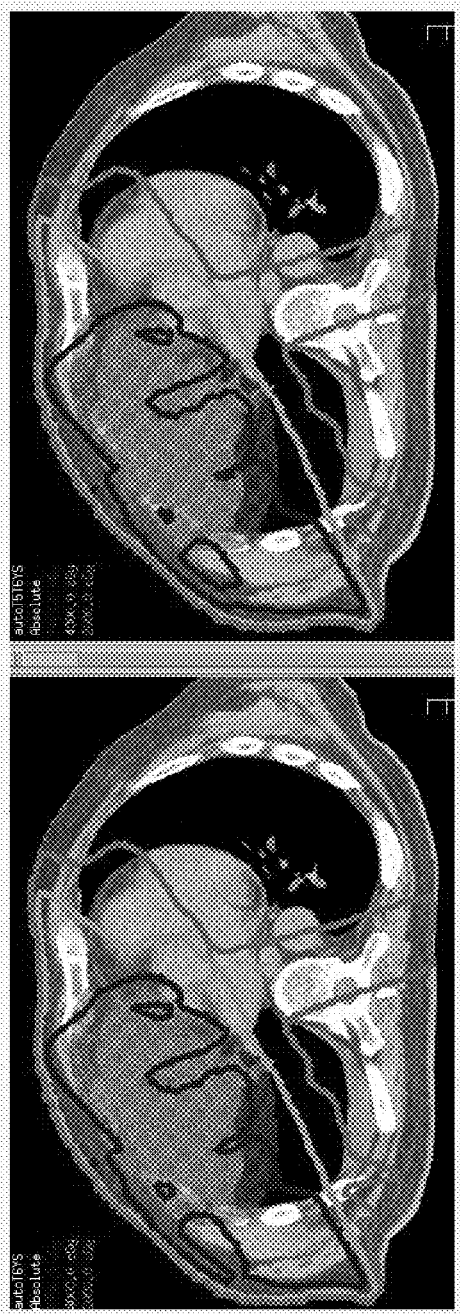
FIG. 6B shows corresponding tissue cross-sections and selective iso-dose curves (7400 cGy, 4000 cGy and 2000 cGy) comparing the deliverable and unconstrained methods.
Figure 7A:
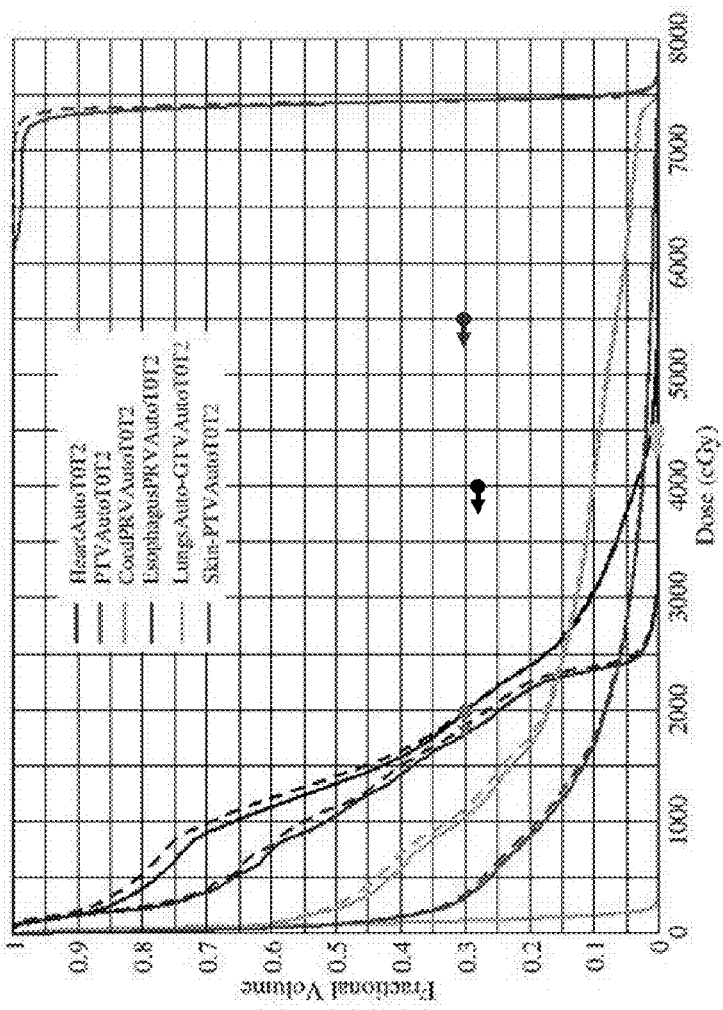
FIG. 7A shows DVH from the least agreement case, whose score ratio was 18.77, where two sets of DVH show some discrepancy.
Figure 7B:
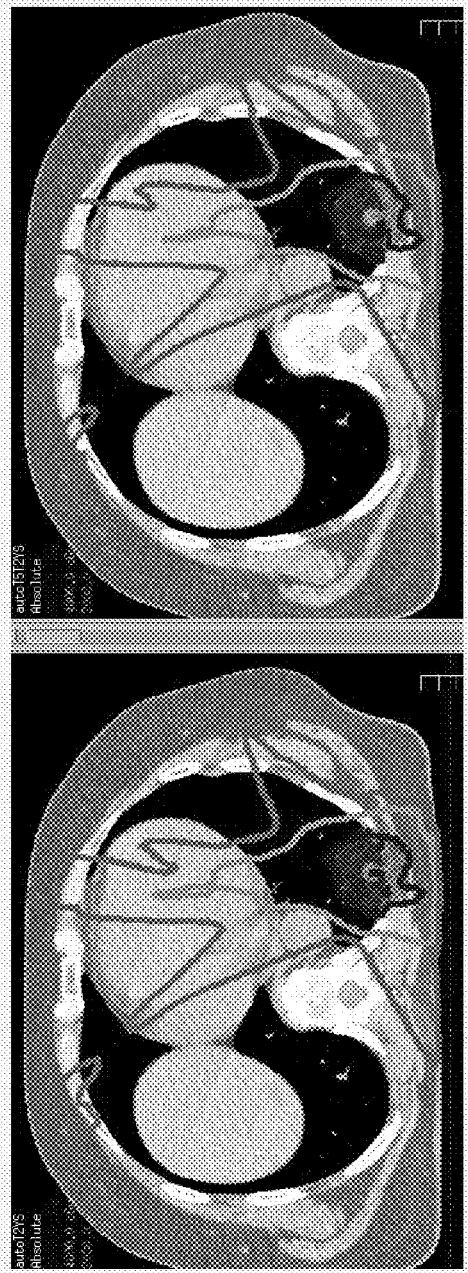
FIG. 7B shows corresponding tissue cross-sections and selective iso-dose curves (7400 cGy, 4000 cGy and 2000 cGy) comparing the deliverable and unconstrained methods.
Figure 8A:
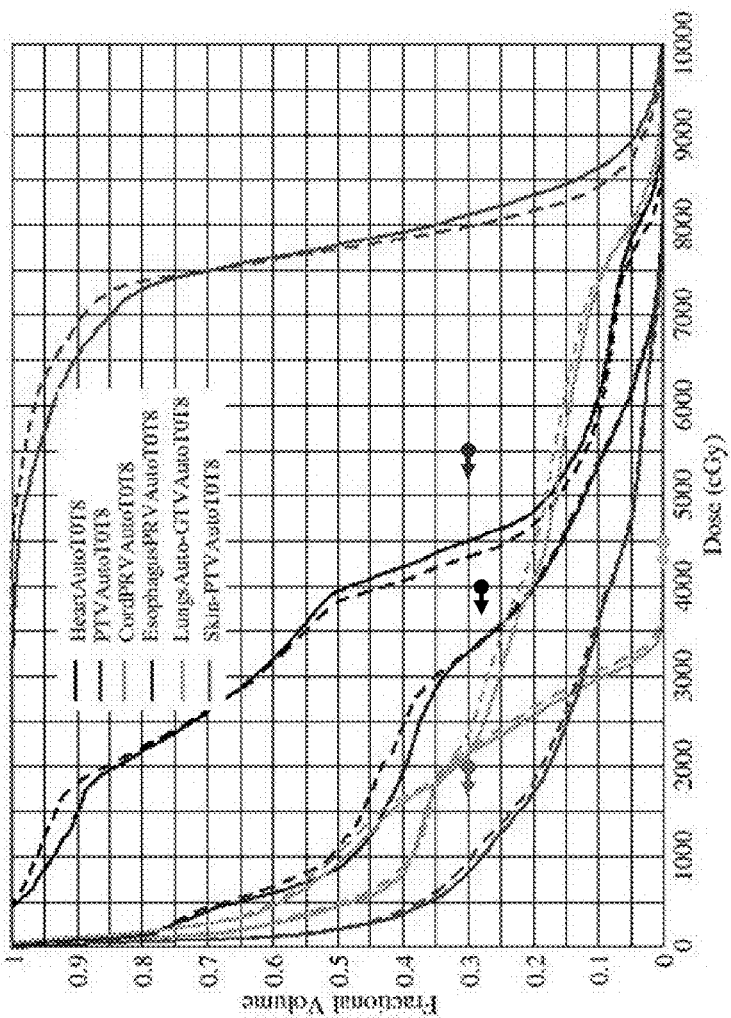
FIG. 8A shows DVH from the case with the largest PTV $D_{95\%}$ and lung $D_{mean}$ differences.
Figure 8B:
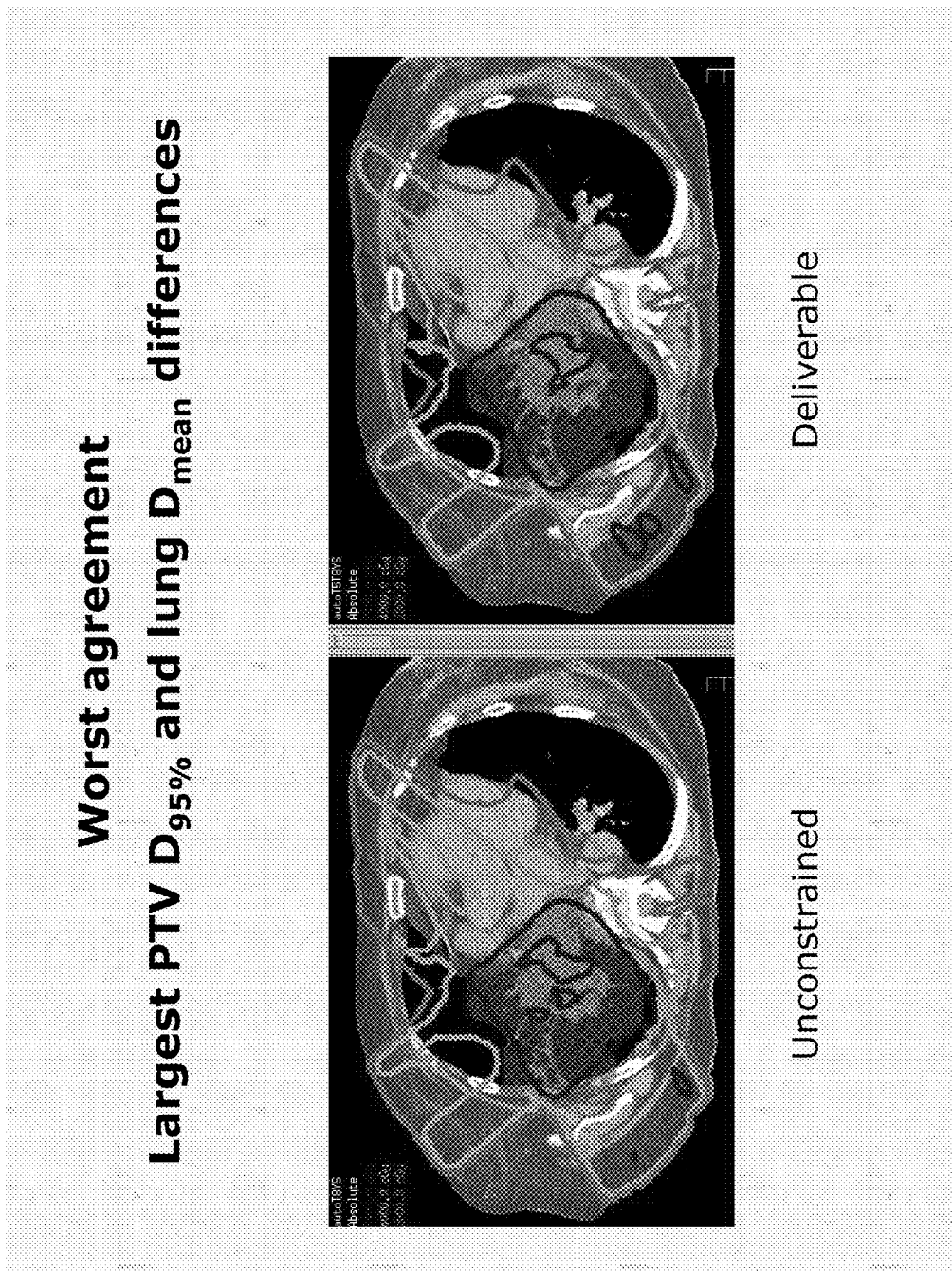
FIG. 8B shows corresponding tissue cross-sections and selective iso-dose curves (7400 cGy, 4000 cGy and 2000 cGy) comparing the deliverable and unconstrained methods.

Dose-volume metrics shown in Table A were computed from dose-volume histograms (DVHs) for each phase for each patient, as shown in FIG. 5. Note that the Y-axis "Score" in FIG. 5 is an indicator for plan quality as a single number, which takes into account the actually achieved dose distribution for planning target volume (PTV) and organs at risk (OARs) after plan optimization, relative to the initially given constraints. The smaller the score, the better the plan. Solid curves are from deliverable method and dashed curves are from unconstrained method.

Table A shows the mean and standard deviation of the dose-volume metric ratios averaged over each of nine 4D CT phases for each of twelve patients, and p-values testing whether the deliverable and unconstrained distributions are statistically different.

A Specific Embodiment of the Invention

To incorporate the MLC leaf motion constraints into 4D IMRT planning using DMLC, this embodiment is focused on a simplification of rigid body target translation. Only target motion along the MLC leaf motion direction is considered, whereas target motion perpendicular to the MLC leaf motion caused by target deformation/rotation and motion nonlinearity/hysteresis is ignored. This approach yields a planning scheme that is not optimal but, importantly, is deliverable with currently available technology. For comparison, a three-dimensional (3D) optimal scheme also is shown, in which the dose distribution in each phase of the 4D CT scan is independently optimized. A given phase represents what could be achieved using respiratory gating. The 3D optimal approach accounts for target deformation/rotation and motion nonlinearity/hysteresis but ignores MLC leaf motion constraints and thus is deliverable only if the MLC leaf velocity is infinite.

Formalism for 4D IMRT Planning Optimization

The aim of 4D IMRT planning optimization for DMLC tumor tracking is to find the deliverable leaf sequence, L(MU, θ), as a function of monitor unit, MU, and respiratory phase, θ, to satisfy $\min\{f[D(L(MU,\theta))]\}$, where $f$ is a mathematical cost function representation of a clinical objective, and D is the prescribed dose distribution:

$$D = \sum_{\theta=0}^{P} \lambda_\theta D_\theta(I(\theta), I_{ref}, u(\theta), L(MU, \theta)), \tag{1}$$

where $\lambda_\theta$ is time spent per each phase, $D_\theta$ is dose for a given phase, I is a 4D CT image of anatomy where I(θ) represents a given 3D instance for phase θ and $I_{ref}$ the image used for dose summation, and u is a displacement vector field computed using deformable registration mapping images from a given to the reference phase. To obtain $D_\theta$, the dose is computed on I(θ) on the basis of L(MU,θ) and then deformed to $I_{ref}$ using u(θ).

A deliverable 4D IMRT planning method to solve Eq. (1) proposed in this study is to account for rigid body target motion along the MLC leaf direction only, as well as to ensure that MLC leaf motion does not exceed the maximum leaf

TABLE A

| | Planning Target Volume (PTV) | | Lungs-GTV | | Spinal cord |
|---|---|---|---|---|---|
| | $(D_{mean})_{unc}^{del}$ | $(D_{95\%})_{unc}^{del}$ | $(D_{mean})_{unc}^{del}$ | $(V_{20})_{unc}^{del}$ | $(D_{0.1\%})_{unc}^{del}$ |
| Mean | 1.002 | 0.991 | 1.005 | 1.006 | 1.003 |
| (stdev) | (0.004) | (0.018) | (0.016) | (0.025) | (0.035) |
| (min, max) | (0.989, 1.015) | (0.905, 1.012) | (0.957, 1.037) | (0.946, 1.082) | (0.929, 1.196) |
| p-value | 0.13 | 0.09 | 0.48 | 0.46 | 0.46 |

| | Esophagus | | Heart | | Thorax-PTV |
|---|---|---|---|---|---|
| | $(D_{mean})_{unc}^{del}$ | $(V_{55})_{unc}^{del}$ | $(D_{mean})_{unc}^{del}$ | $(V_{40})_{unc}^{del}$ | $(D_{mean})_{unc}^{del}$ |
| Mean | 1.012 | 1.030 | 1.009 | 0.978 | 1.003 |
| (stdev) | (0.038) | (0.047) | (0.032) | (0.211) | (0.014) |
| (min, max) | (0.926, 1.204) | (0.896, 1.208) | (0.902, 1.095) | (0.000, 1.266) | (0.962, 1.028) |
| p-value | 0.44 | 0.44 | 0.47 | 0.39 | 0.48 | velocity (22). The deliverable method finds the deliverable leaf sequence on the reference phase, $L(MU,\theta_{ref})$, to satisfy $\min\{f[D(L(MU,\theta_{ref}))]\}$, where $D=D_{\theta_{ref}}(I_{ref}L(MU,\theta_{ref}))$ and $\theta_{ref}$ is the reference phase. For the rigid body target translation, the solutions for other phases become $L(MU,\theta)=L(MU,\theta_{ref})+g(\theta)$, where $g(\theta)$ is the target centroid displacement from the reference phase to phase $\theta$ along the major axis of target motion in a given beam's eye view (BEV).

A benchmark method is a 3D optimal method, which finds the optimal leaf sequence, $L(MU,\theta)$, to satisfy $\min\{f[D_\theta(L(MU,\theta))]\}$ for each phase independently.

4D CT Data and Patient Characteristics

The 4D CT data of 12 lung cancer patients acquired on a 16-slice CT scanner in a cine mode (GE Healthcare Technologies, Waukesha, Wis.) were used. The acquisition was performed as a part of an institutional review board-approved study (protocol 00-202) at the University of Texas M. D. Anderson Cancer Center. On the base of the respiratory signal from a respiration monitoring system (RPM; Varian Medical Systems, Palo Alto, Calif.), the respiratory cycle was divided into 10 phases of equal duration, with Phase 0 representing end-inhale and Phase 5 approximately end-exhale. The tumor classifications ranged from T1N0 to T4N0, and tumors were located in the upper lobes for 9 patients and in the lower lobes for 3 patients with peripheral (3 patients) and central (9 patients) tumor localizations. The means of gross tumor volume (GTV) and GTV centroid motion range were 49.2 cm$^3$ and 0.7 cm, respectively (Table 1).

Contouring and IMRT Planning

Contouring and planning were performed using a commercially available planning system (Pinnacle 7.9; Philips Medical Systems, Milpitas, Calif.). On the base of the manually segmented contours on Phase 0, the contours on the other 9 phases of the 4D CT scan were automatically generated using large deformation diffeomorphic image registration. The GTV was expanded by an 8-mm margin to yield the clinical target volume (CTV), and a 5-mm margin was added to create the planning target volume (PTV). The prescribed dose to PTV was 74 Gy, and beam arrangements were six coplanar, non-opposed, predominantly anterior-posterior, with beam angles adjusted depending on the tumor locations.

Detailed Description of the Drawings for this Specific Embodiment

Figure 10:
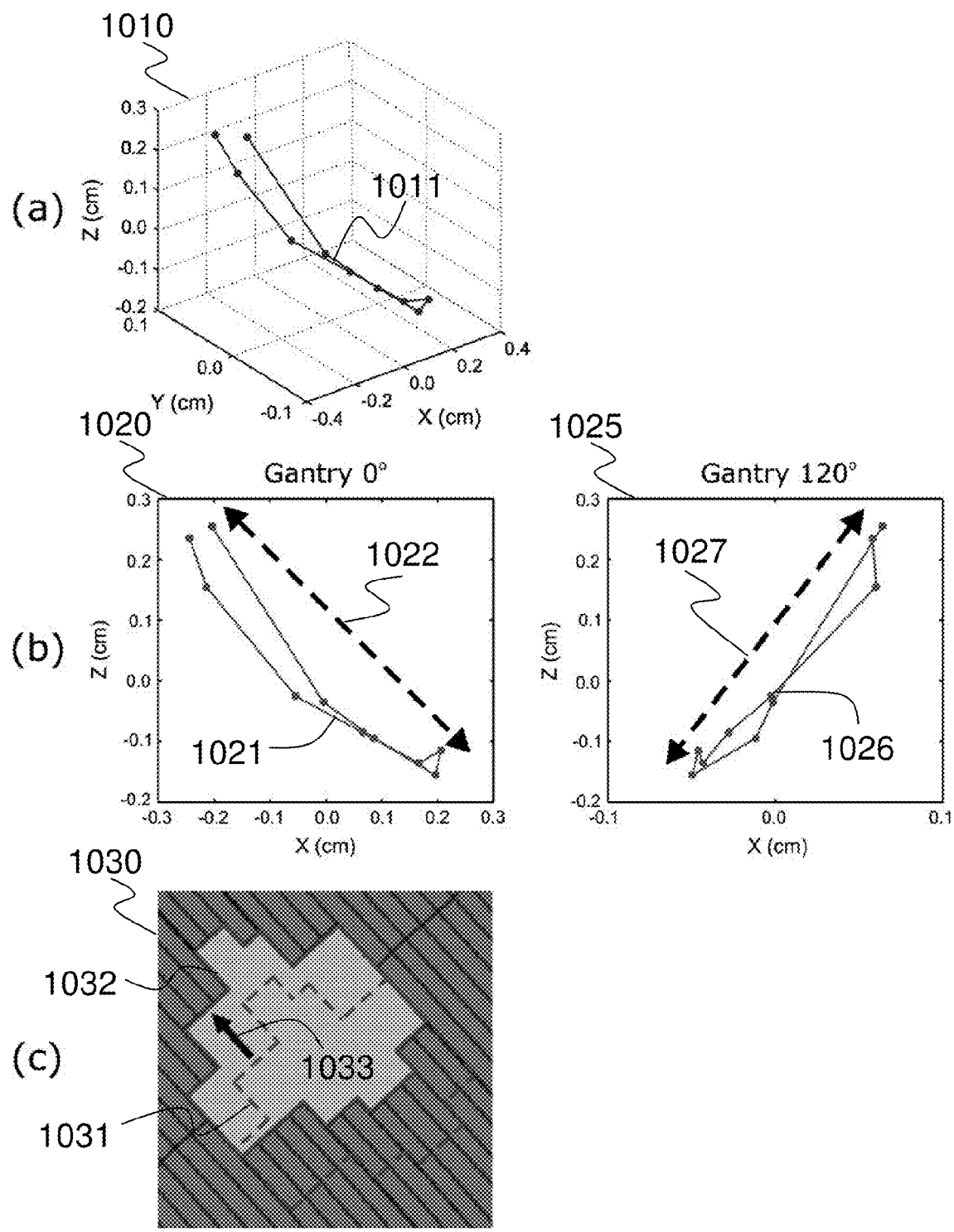
FIG. 10 is a series of diagrams showing determination of the major axis of target motion.

FIG. 10 shows determination of the major axis of target motion. (a) 1010 is a representation of the target motion 1011 in three dimensions. (b) (1020 and 1025) illustrates different two-dimensional motion (1021 and 1026, respectively) in the beam's eye view (BEV) of different beam angles, such as gantry angles of 0° (1020) and 120° (1025). On the basis of the target positions in a given BEV, the major axis (dashed arrows 1022 and 1027) of target motion is automatically determined for each beam: collimator angles are 41° and 106° for the gantry of 0° and 120°, respectively. Diagram (c) 1030 shows that for the gantry angle of 0° in (b) 1020, the collimator is rotated by 41° to align multileaf collimator leaf motion parallel to the major axis 1022. For a given phase plan, a beam aperture is translated (as indicated by arrow 1033) from the reference (dashed line 1031) to a given (solid line 1032) phase by the difference in the target centroid position between the two phases, as seen in the BEV.

Figure 11:
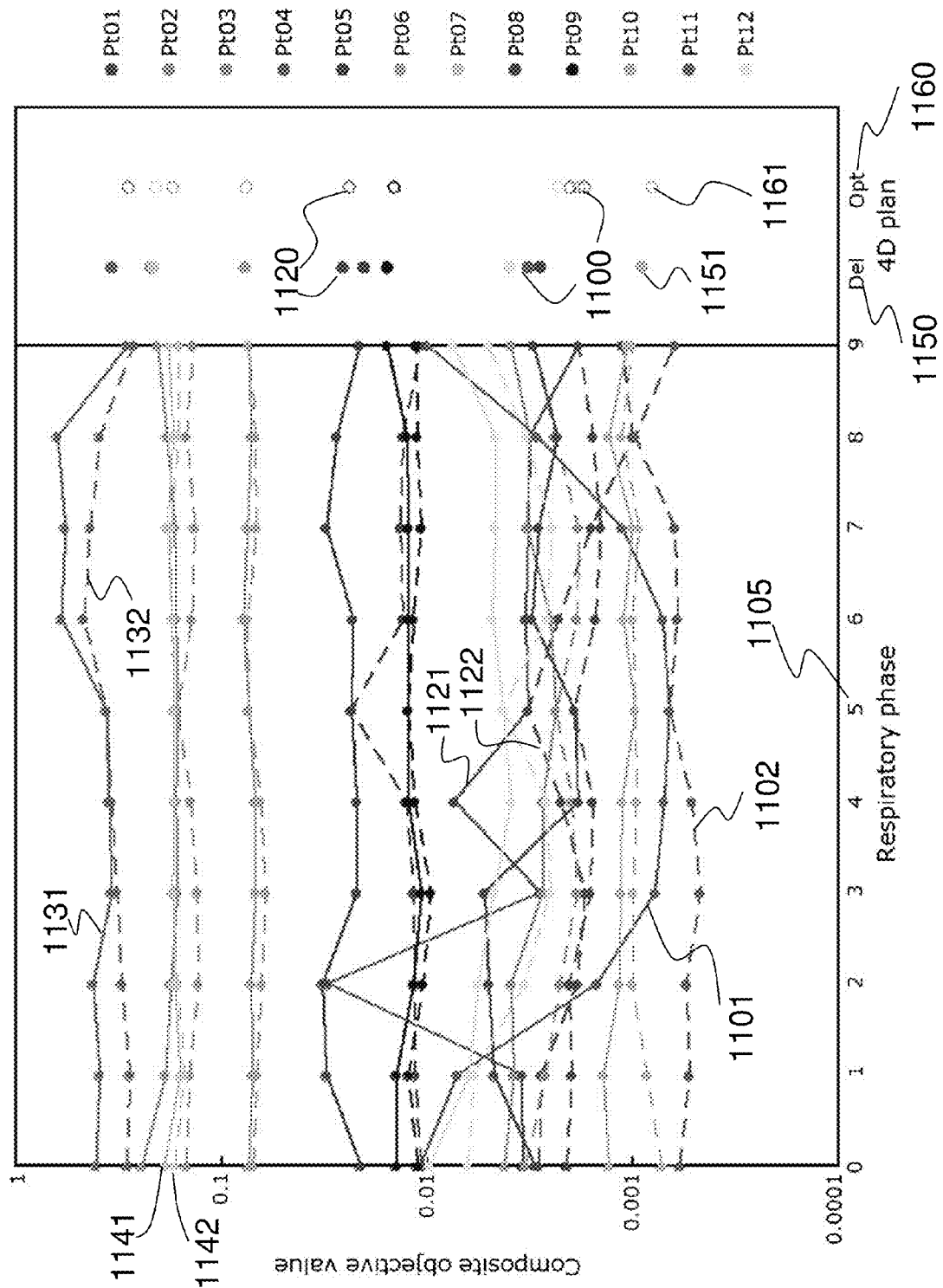
FIG. 11 shows composite objective values of individual phase plans using the deliverable and three-dimensional (3D) optimal methods and those of four-dimensional (4D) plans using the deliverable and 3D optimal methods for each patient.

FIG. 11 shows composite objective values of individual phase plans using the deliverable (solid line, e.g. 1101) and three-dimensional (3D) optimal (dashed line, e.g. 1102) methods and those of four-dimensional (4D) plans using the deliverable (Del 1150, filled circles, e.g. 1151) and 3D optimal (Opt 1160, empty circles, e.g. 1161) methods for each patient. The smaller the value, the better the plan. The two methods have identical objective values for Phase 5 1105, which is the reference exhale phase. For the other phases, the 3D optimal method always yields better plans. The 4D composite objective values for each method are similar to the average values over individual phase plans per patient.

Figure 12:
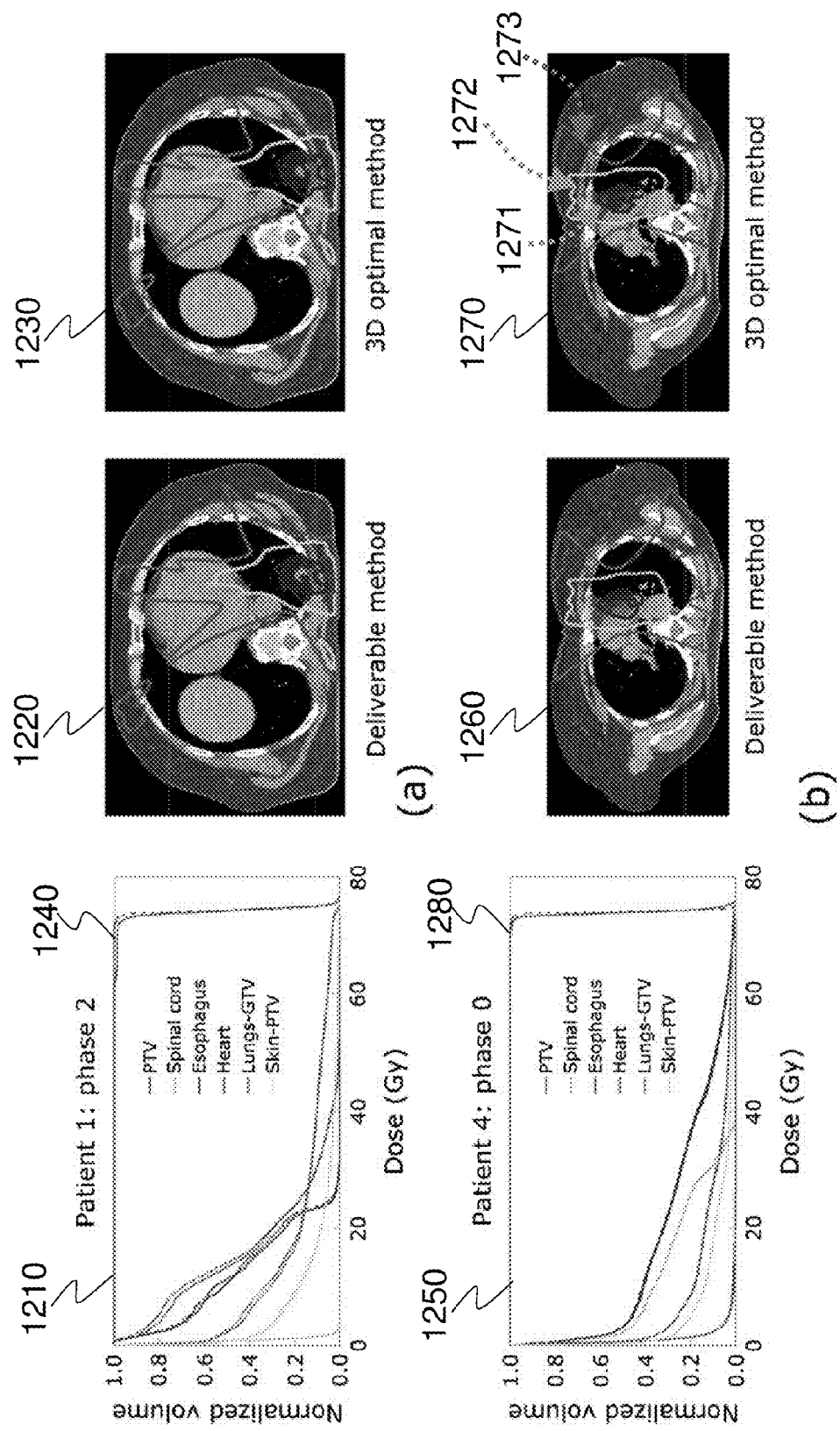
FIG. 12 shows dose-volume histograms and isodose distributions of individual phase plans showing discrepancy in the composite objective values between the two methods.

FIG. 12 shows dose-volume histograms (DVHs 1210 and 1250) and isodose distributions of individual phase plans showing discrepancy in the composite objective values between the two methods (deliverable method 1220 and 1260, and 3D optimal method 1230 and 1270): (a) the second-worst agreement case (objective value ratio of 18.1) due to the artifacts in the 4D CT scan; and (b) the worst agreement case (objective value ratio of 18.4) due to significant variation in tumor volume during the respiratory cycle. Solid DVHs are for the deliverable method and dashed for the 3D optimal method. The planning target volume (PTV) is shaded in red (1240 and 1280); blue isodose curves (e.g. 1271) indicate 74 Gy, green (e.g. 1272) 40 Gy, and pink (e.g. 1273) 20 Gy.

Figure 13:
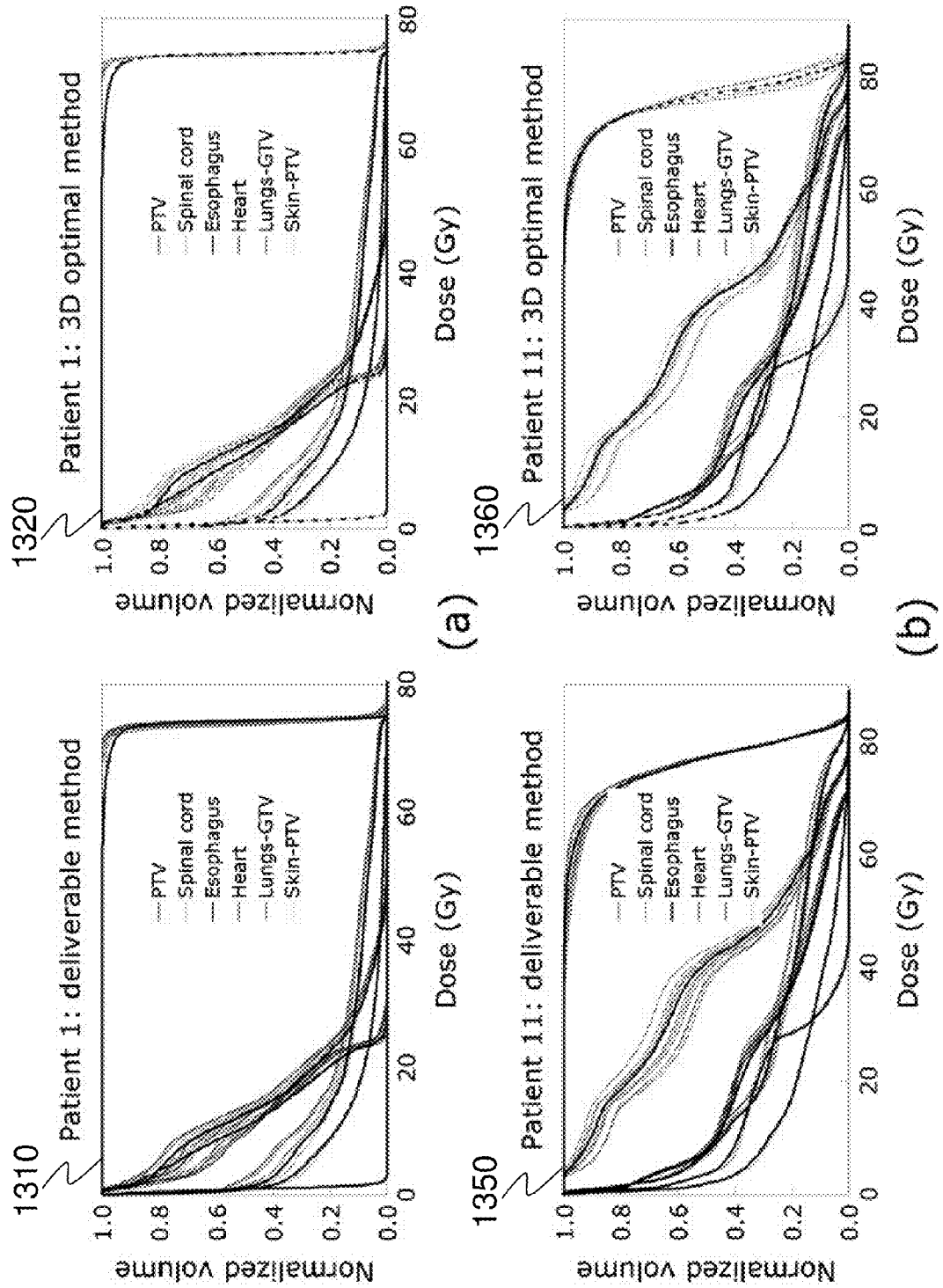
FIG. 13 shows dose-volume histograms (DVHs) of all 10 individual phase plans for each of two patients (Patient 1 and Patient 11).

FIG. 13 shows dose-volume histograms (DVHs) of all 10 individual phase plans for each of two patients (Patient 1 and Patient 11) with four-dimensional (4D) plans (black thick curves) for the deliverable (left column, 1310 and 1350) and three-dimensional (3D) optimal (right column, 1320 and 1360) methods: (a) significant phase-to-phase variation with degraded planning target volume (PTV) coverage in 4D plans; and (b) significant phase-to-phase variation, but with reasonable DVHs (about the averages over individual phase plans) in 4D plans. Solid DVHs are for the deliverable method and dashed for the 3D optimal method.

Figure 14:
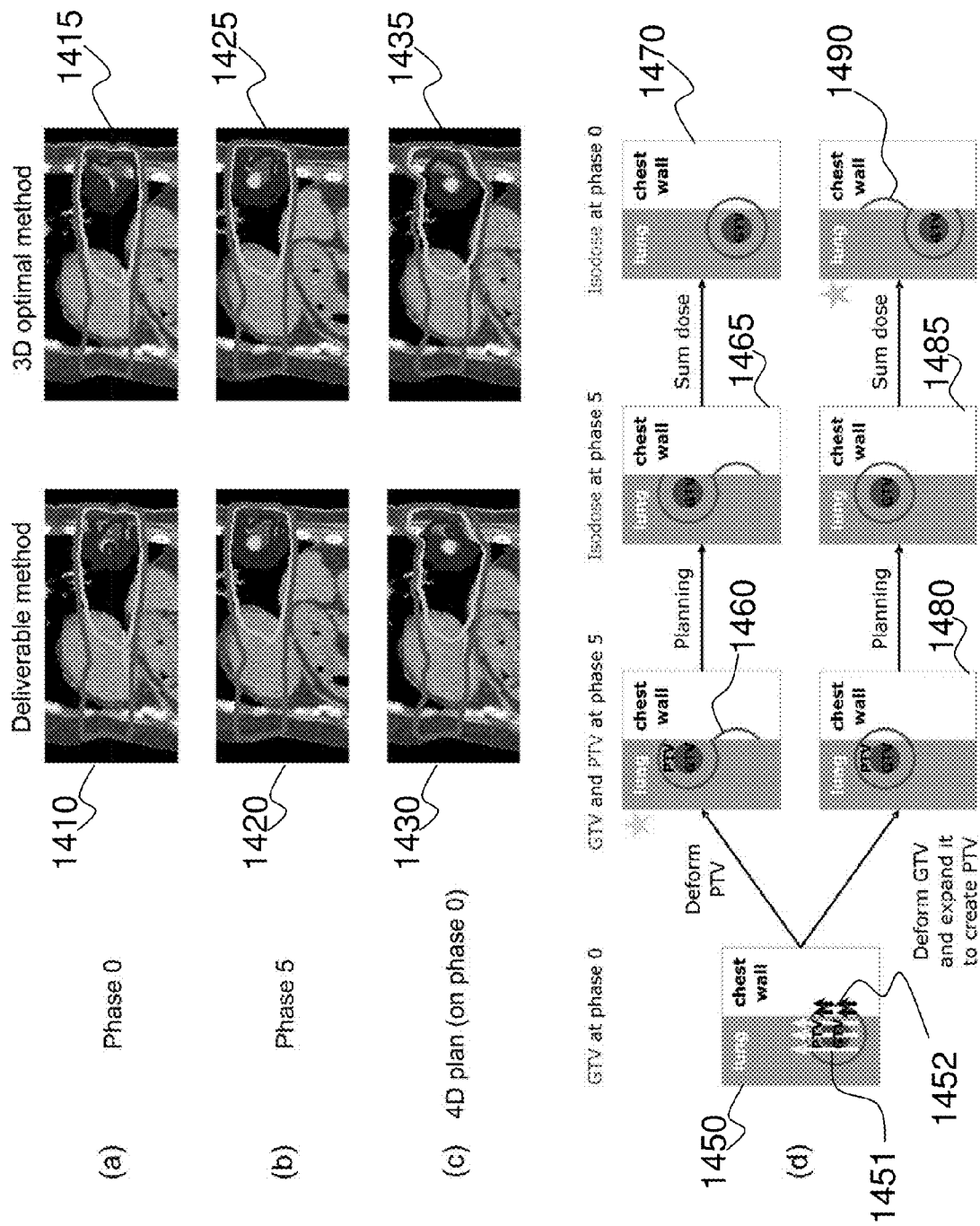
FIG. 14 shows isodose distributions for (a) Phase 0 plans and (b) Phase 5 plans), and (c) four-dimensional (4D) plans (on Phase 0 CT image) using the two methods (deliverable and 3D optimal) in a sagittal view for Patient 1.

FIG. 14 shows isodose distributions for (a) Phase 0 plans (1410 and 1415) and (b) Phase 5 plans (1420 and 1425), and (c) four-dimensional (4D) plans (on Phase 0 CT image; 1430 and 1435) using the two methods (deliverable and 3D optimal) in a sagittal view for Patient 1. Note that Phase 5 plans are identical for both methods. Whereas the dose distributions of Phase 0 and Phase 5 plans look reasonable (a, b), the 4D plans have inconsistent dose distributions (c) for both methods. (d) This is due to large gradients of the deformation vector field across the planning target volume (PTV). Because the vector field is large in the lungs (e.g. 1451) and small in the chest wall (e.g. 1452), deforming the PTV generates unrealistic appearance of the PTV after deformable image registration (as shown in 1460). Deforming the gross tumor volume (GTV) and expanding it to create the PTV results in inconsistent dose distributions after deformable dose summation (as shown in 1490).

Figure 15:
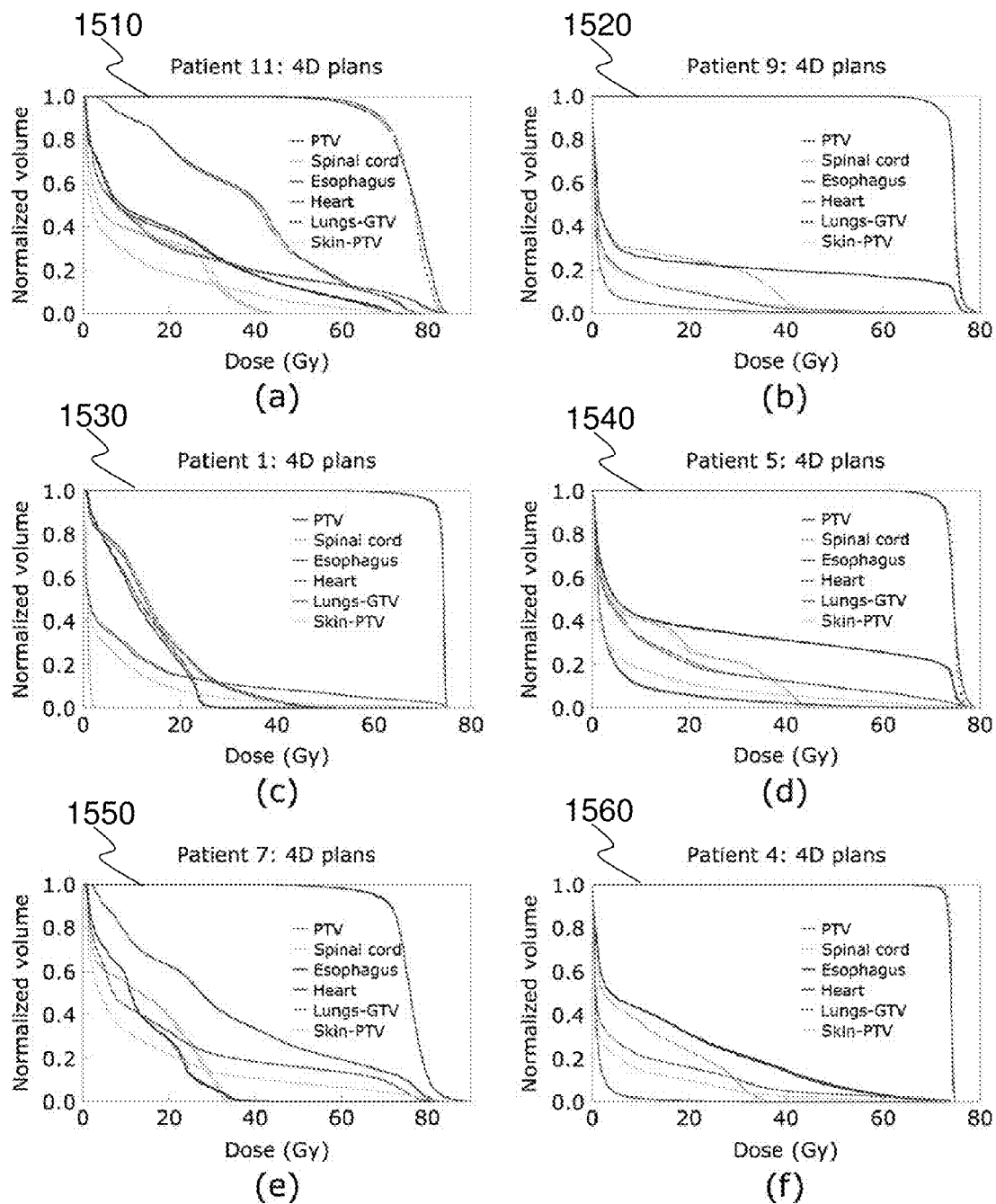
FIG. 15 shows dose-volume histograms (DVHs) of four-dimensional (4D) plans using the two methods for the patients with various tumor characteristics.

FIG. 15 shows dose-volume histograms (DVHs) of four-dimensional (4D) plans using the two methods for the patients with various tumor characteristics: (a) most hysteresis (0.35 cm); (b) least hysteresis (0 cm); (c) most motion (2.1 cm); (d) least motion (0.1 cm); (e) largest volume (323.6 cm$^3$); and (f) smallest volume (1.0 cm$^3$) Solid DVHs are for the deliverable method and dashed for the three-dimensional (3D) optimal method.

Methods of the Deliverable and 3D Optimal IMRT Planning on the 4D CT Scans

The deliverable 4D IMRT planning method involves four steps for each patient, as will now be shown with reference to FIG. 3. From Steps 1 through 3, individual phase plans are created, and in Step 4 deformable dose-summed 4D plans are created.

Step 1 (320). The appropriate beam angle arrangement for an IMRT plan is determined. The target centroid position for each phase is quantified from a 4D CT image set. The major axis of target motion is determined in each BEV. Then, for each beam, the collimator is rotated to align MLC leaf motion parallel to the major axis. FIG. 10 shows this key step in the deliverable 4D IMRT planning method. The same target motion in 3D, shown in (a) 1010 of FIG. 10, has different two-dimensional motion in the BEVs of different beam angles, as shown in (b) 1020 and 1025 of FIG. 10. On the basis of the target positions in a given BEV, the major axis (dashed arrows 1022 and 1027) of target motion is automatically determined for each beam using a least-squares fit.

Step 2 (330). For the reference phase (end-exhale was used as the most stable phase during respiration, but in general the method does not require a particular phase—or any phase—as a reference), an appropriate IMRT plan is created with the rotated collimator, creating MLC leaf positions for each beam.

Step 3 (340). For each of the other phases, an IMRT plan is created by copying the MLC leaf positions for the reference phase and translating them by the relative displacement of target centroid for each phase, while keeping the collimator angle for each beam the same. For example, for a given phase plan, a beam aperture can be shifted from the reference phase (dashed line 1031 in FIG. 10) to the given phase (solid line 1032) by the difference 1033 in the target centroid position between the two phases, as seen in the BEV. All 10 individual phase plans for a given patient using the deliverable method are exactly the same except for the MLC leaf positions translated.

Step 4 (350). For each patient, a deformable dose-summed 4D plan is created by accumulating the resultant doses from all individual phase plans on Phase 0 CT image using deformable dose summation.

For comparison, the 3D optimal method, which is the same as the deliverable method except for Step 3 and Step 4, may be applied. To create plans for the other phases 345, with the same IMRT beam angle arrangement and collimator angles as the deliverable plans, the 3D optimal method independently optimizes an IMRT plan on each phase of the 4D CT images. All 10 individual phase plans for a given patient using the 3D optimal method can be different except for beam and collimator angles.

The deliverable method may be compared with the 3D optimal method (at 355) using composite objective values and dose-volume evaluation metrics derived from the dose-volume histogram (DVH). The composite objective value, a single number, is an indicator of plan quality that takes into account the actually achieved dose distribution for the PTV and organs at risk (OARs) after plan optimization, relative to the initial constraints. The smaller the composite objective value, the better the plan. For individual phase plans, the mean and SD of dose-volume metric ratios are averaged over all 10 phases for all 12 patients:

$$\overline{X_{opt}^{del}} = \frac{\sum_i^M \sum_j^N X_{del}^{i,j} / X_{opt}^{i,j}}{M \cdot N} \text{ and}$$

$$\sigma_{\overline{X_{opt}^{del}}} = \sqrt{\frac{\sum_i^M \sum_j^N (X_{del}^{i,j} / X_{opt}^{i,j} - \overline{X_{opt}^{del}})^2}{M \cdot N}},$$

where X is a dose-volume metric computed from the DVHs of plans using the deliverable ($X_{del}$) or 3D optimal ($X_{opt}$) methods, i is a patient number, and j is a phase number. For 4D plans, those are averaged over all 12 patients:

$$\overline{X_{opt}^{del}} = \frac{\sum_i^M X_{del}^i / X_{opt}^i}{M} \text{ and } \sigma_{\overline{X_{opt}^{del}}} = \sqrt{\frac{\sum_i^M (X_{del}^i / X_{opt}^i - \overline{X_{opt}^{del}})^2}{M}}.$$

A one-tailed Student's t-test with the null hypothesis of $H_0: X_{opt} = X_{del}$ and the alternative hypothesis of $H_A: X_{opt} > X_{del}$ can be used to evaluate whether the two methods are statistically different (statistically different if p<0.05).

Results of Specific Embodiment

Individual Phase Plans

FIG. 11 shows the composite objective values of individual phase plans using the deliverable and 3D optimal methods for each patient. The two methods have identical objective values for Phase 5 (1105). For the other phases, the 3D optimal method always yields smaller values (better plan quality). Variation in plan quality is generally larger for phase-to-phase compared with that for method-to-method.

Patient 1 shows significant discrepancy in the composite objective values between the two methods (1121 and 1122 in FIG. 11) for some phases. There are artifacts in the 4D CT image set for this patient, including division of the tumor into two parts for three phases. The artifacts deteriorate target coverage when the deliverable method is used, resulting in discrepancy in both PTV coverage and OAR sparing between the two methods, as shown in (a) in FIG. 12. FIG. 12 shows the DVHs 1210 and isodose distributions 1220 for Patient 1, which illustrates the second-worst agreement case in terms of the composite objective values (value ratio of 18.1). Patient 4 also shows significant discrepancies in the composite objective values between the two methods (1101 and 1102 in FIG. 11) throughout the phases, which is explained by the largest variation in tumor volume during the respiratory cycle. Even though Phase 0 plans using the two methods for Patient 4 show the worst agreement in terms of the composite objective value (value ratio of 18.4), there is discrepancy only in the DVHs of the PTV (1280 in FIG. 12). The 74-Gy isodose curve does not cover the whole PTV in the deliverable plan, unlike in the 3D optimal plan (1271 in FIG. 12). Patient 7, whose tumor has almost no motion during respiration, shows the best agreement of the composite objective values between the two methods (1141 and 1142 in FIG. 11) for all phases.

FIG. 11 also shows phase-to-phase variation in plan quality. Whereas the composite objective values for the 3D optimal method do not vary much from phase to phase, those for the deliverable method do vary. There is significant phase-to-phase variation in plan quality using the deliverable method for Patients 1 (1121) and 4 (1101). Again, Patient 1 has artifacts in the 4D CT images, and Patient 4 has the largest tumor volume variation. Patient 4 also shows a trend in that the farther the respiratory phases are from reference Phase 5, the worse the deliverable plan quality becomes. The significant variation in tumor volume causes inferior PTV coverage in the deliverable plans, especially for the phases further away from reference Phase 5. FIG. 13 shows the DVHs of all 10 individual phase plans using the two methods (1310 and 1320) for Patient 1. Although the composite objective values do not vary significantly, there are phase-to-phase variations of the DVHs in the 3D optimal plans, especially for the OARs.

Because the composite objective value is a numerical indicator of plan quality and does not indicate the plan details, a patient showing the most discrepancy in the DVHs between methods and between phases is chosen by visually inspecting the DVHs. Despite relatively good agreement of plan quality (1131 and 1132 in FIG. 11), Patient 11 shows the most discrepancy in the DVHs between methods and between phases, as shown in 1350 and 1360 in FIG. 13, because the tumor shows the most hysteresis during respiration, the second biggest volume, and the second most motion. These attributes also cause the largest difference in PTV $D_{95\%}$ (dose received by 95% of the PTV) and lung $D_{mean}$ (mean dose to the lungs) between the two methods.

Table 2 shows dose-volume metric ratios of individual phase plans. All mean values of the dose and volume metric ratios are very close to 1.00, indicating that the deliverable and 3D optimal methods yield similar dose-volume characteristics. No evaluated dose-volume metric is statistically different between the methods ($p>0.05$ for all metrics compared), whereas PTV coverage shows more variation than OARs.

Deformable Dose-Summed 4D Plans (4D Plans)

FIG. 11 also shows the composite objective values of 4D plans using the two methods for each patient. The 3D optimal method always yields better plans. The 4D composite objective values for each method are similar to the average values over individual phase plans per patient.

However, 4D plans for Patient 1 (1120 in FIG. 11) are significantly worse than individual phase plans for both methods. Degraded 4D plans for Patient 1 also are evident in FIG. 13 (1310 and 1320), mainly owing to inferior PTV coverage. FIG. 14 shows the isodose distributions of individual phase plans on Phase 0 (1410, 1415) and Phase 5 (1420, 1425), as well as 4D plans (1430, 1435) for Patient 1. Although the dose distributions for Phase 0 and Phase 5 plans look reasonable, 4D plans have inconsistent dose distributions for both methods. This is explained by large gradients of the deformation vector field across the PTV. Because the tumor of Patient 1 is next to the chest wall and moves 2.1 cm, the vector field, which differs significantly across the PTV, is used for deformable image registration and dose summation. As shown schematically in FIG. 14, the vector field tends to be large in the lungs (1451) and small in the chest wall (1452). As a result, some portion of the PTV (in the chest wall) deforms differently from its other portion (in the lungs). Thus, deforming the PTV (as shown in 1460, 1465, and 1470) differs from deforming the GTV and expanding it (as shown in 1480, 1485, and 1490) to create the PTV, because the former may generate unrealistic appearance of the PTV after deformable image registration (see 1460 in FIG. 14). However, when the dose is deformed back to Phase 0, the latter may result in inconsistent dose distributions after deformable dose summation (see 1490 in FIG. 14). Because this occurs in both methods, the composite objective values for the two 4D plans are similar (1120 in FIG. 11) and the DVHs do not show significant discrepancy, especially for PTV coverage, as shown in 1530 in FIG. 15.

On the other hand, Patient 4 shows the largest difference in the composite objective values between the two 4D plans (1100 in FIG. 11), whereas the composite objective value for each 4D plan is an average of individual phase plans, respectively. Again, this is due to the most variation in tumor volume, which results in poor PTV coverage in the deliverable plans, as shown in 1560 in FIG. 15.

As shown in FIG. 13 (1350 and 1360), Patient 11 has significant phase-to-phase variation in the DVHs for individual phase plans but shows reasonable DVHs for the two 4D plans, each of which is an approximate average of the DVHs for individual phase plans. The composite objective values for the two 4D plans are better than the average of those values over individual phase plans (1131 and 1132 in FIG. 11). Between the two 4D plans, however, Patient 11 shows the most discrepancy in the DVHS, as shown in 1510 in FIG. 15. The tumor of this patient has the most hysteresis (0.35 cm), whereas Patient 9 with the least hysteresis (0 cm) shows two DVH sets on the top of each other, indicating good agreement between the two 4D plans, as shown in 1520 in FIG. 15. Patient 9 actually shows the best agreement between the two methods.

In terms of tumor motion, both of the patients with the most motion (2.1 cm) (see 1530 in FIG. 15) and the least motion (0.1 cm) (see 1540 in FIG. 15) show discrepancies in the DVHs. In terms of tumor volume, both of the patients with the largest tumor volume (323.6 cm$^3$) (1550 in FIG. 15) and the smallest tumor volume (1.0 cm$^3$) (1560 in FIG. 15) show relatively good agreement in the DVHs.

Table 3 shows dose-volume metric ratios of 4D plans. As in Table 2, all mean values are very close to 1.00, indicating that two methods yield similar dose-volume characteristics. Again, no evaluated dose-volume metric is statistically different between the methods ($p>0.05$ for all metrics compared), whereas PTV coverage shows more difference than OARs. The difference in PTV coverage between the two methods is smaller than that for individual phase plans.

Discussion of Specific Embodiment

An "ideal" 4D IMRT planning would be one optimized over the continuous motion of target and surrounding normal tissues, which may be deliverable, and a methodology for developing such a solution is described in the General Embodiment section below. However, the above described and evaluated Specific Embodiment provides a "deliverable" 4D IMRT planning method. The reason for taking this approach is that it provides a feasible solution that uses current planning technology and thus has a clear path to clinical application. Though this approach is clearly not optimal, given the assumptions made, it has been shown that tumor tracking yields better results than the gated technique, and both methods provide improved treatment compared with the motion-inclusive technique.

The planned clinical application of the Specific Embodiment involves integrating the linear accelerator with a real-time target position monitoring system. As the target position information is obtained, the appropriate corrections are made to the leaf positions in real time. A "3D optimal" method that involved an independent 3D IMRT optimization for each phase of the 4D CT scan also is proposed as a benchmark method. It is important to note that the sum of individually optimized dose distributions does not guarantee an optimal dose distribution because $\min\{f[D(L(MU,\theta))]\}$ is a subset of $$\sum_\theta \min\{f[D_\theta(L(MU,\theta))]\}.$$

"Deliverable" means that the plan does not have MLC leaf motion exceeding the maximum velocity of the MLC leaves. The average maximum leaf velocity at the isocenter plane ranges from 3.3 to 3.9 cm/s. In this series of patients, this velocity is exceeded by only 3 of 10 phase transitions in 1 of 12 patients. In Patient 1, the displacement of 2.1, 1.6, and 1.6 cm was observed in subsequent phases (0.4 s apart), corresponding to the velocities of 5.3, 4.0, and 4.0 cm/s for a 4-s period, respectively. A beam hold mechanism will be a part of DMLC tracking implementation. It is not advisable to follow sharp position changes or coughing, providing that the beam hold is not applied so frequently as to significantly affect efficiency, which in this case would be 100% for 11 of 12 patients and 70% for Patient 1. The collimator rotation is not planned to be changed on a daily basis. The deliverable implementation would account for some motion perpendicular to the MLC leaf direction by readjusting the MLC positions on the basis of the plan and the estimated or measured target positions. However, if this algorithm is included in an on-line 4D adaptive therapy strategy, the collimator rotation could be changed day to day.

In addition, the algorithm for collimator rotation and MLC shift is not manufacturer specific. Important MLC parameters required to implement this algorithm are a maximum leaf velocity and a fast secondary position feedback system that allows for real-time control of leaf positions.

As described above, the deliverable and 3D optimal methods were applied to 12 lung cancer patient 4D CT image sets. Two important findings are as follows. First, the deliverable method is dosimetrically robust to the variations of fractional time spent in respiratory phases on a given 4D CT scan. The deliverable method has the same $\lambda$ in Eq. (1) for all phases. Given that the dose distributions of individual phase plans using the deliverable method are very similar to one another (Table 2), the deliverable method would result in the dose distribution close to the planned dose distribution, even when a patient spends more time on one phase (e.g., end-exhale) than other phases during treatment. In addition, for 4D plans, the deliverable method yields dosimetric values statistically similar to those with the 3D optimal method (Table 3). This indicates not only that the deliverable method is dosimetrically robust but also that the target deformation/rotation and hysteresis generally have little dosimetric impact for the 12-patient series studied. For each beam the collimator is rotated to align the MLC leaf motion parallel to the major axis of target motion, which is determined from the target motion in a given BEV. Therefore, the target motion perpendicular to the MLC leaf motion is relatively small (0.13 cm at the most), resulting in negligible impact on plan quality.

However, Patient 11 shows the most discrepancy in DVHs for 4D plans between the two methods (1510 in FIG. 15), indicating that in the presence of hysteresis, the deliverable method is susceptible to plan quality degradation. In terms of target deformation/rotation, Patient 4 shows discrepancy in 4D plans between the two methods, especially for target coverage (1560 in FIG. 15), indicating that target deformation/rotation has some dosimetric impact when the deliverable method is used.

The second important finding is that the PTV concept can cause problems in 4D IMRT planning. The 4D plans for Patient 1 are significantly inferior to individual phase plans for both methods (1121 and 1122 in FIG. 11), mostly owing to PTV coverage (as shown in 1310 and 1320 in FIG. 13). Large gradients of the deformation vector field across the PTV cause unrealistic appearance of the PTV after deformable image registration and inconsistent dose distributions after deformable dose summation (FIG. 14). This problem occurred in 1 of 12 patients in this study. Therefore, care should be taken when there is a possibility that large deformation gradients across the PTV could occur. Eliminating the PTV by using probabilistic planning approaches is one of the solutions.

As for individual phase plans, phase-to-phase variation is generally larger than the difference between the two methods, in terms of plan quality. A more important result is the comparison of 4D plans. The 4D plan quality is similar to average quality over individual phase plans, although three patients have issues. Patient 1 shows degraded 4D plans for both methods due to large deformation gradients across the PTV (1530 in FIG. 15), and Patient 4 shows a degraded deliverable 4D plan due to significant tumor volume variation (1560 in FIG. 15). Given that Patient 11 with the most hysteresis shows the most discrepancy in the DVHs between the two 4D plans (1510 in FIG. 15), whereas Patient 9 with the least hysteresis shows the best agreement (1520 in FIG. 15), having motion hysteresis affects deliverable 4D plans. On the other hand, no marked differences between the two 4D plans with tumor motion or volume indicate that both tumor motion and volume do not have a significant effect on 4D plans using the deliverable method (1530, 1540, 1550 and 1560 in FIG. 15).

A General Embodiment of the Invention

The most general approach to determine the treatment planning for 4D anatomy is to allow MLC leaves to vary as a function of dose delivered (monitor units) and respiratory phase (time), while also allowing for beam on/off at different respiratory phases. When posed in this manner, other approaches to 4D treatment planning become subsets of the gated 4D IMRT solution space, which is shown schematically in FIG. 9. Solution subspace 4D IMRT 920 maintains continuous motion tracking, but does not provide for beam gating. Within this subspace 920 is subspace 4D Conformal RT 930, which has no leaf motion with change in monitor unit, and subspace Motion inclusive IMRT, which has no leaf motion with change in phase. A further solution subspace is Gated IMRT, which has beam gating but no leaf motion with change of phase.

Thus, the main challenge is to solve the gated 4D IMRT planning optimization problem 910. Once this problem is solved, limiting the degrees of freedom (adding additional constraints) and reducing the solution space further to solve for other methods described in FIG. 9 is straightforward.

General Framework

Prior to discussing the formalism of 4D planning optimization problem, it is helpful to define the symbols used in the following equations. Table 4 describes the variables used in this General Embodiment.

Figure 9:
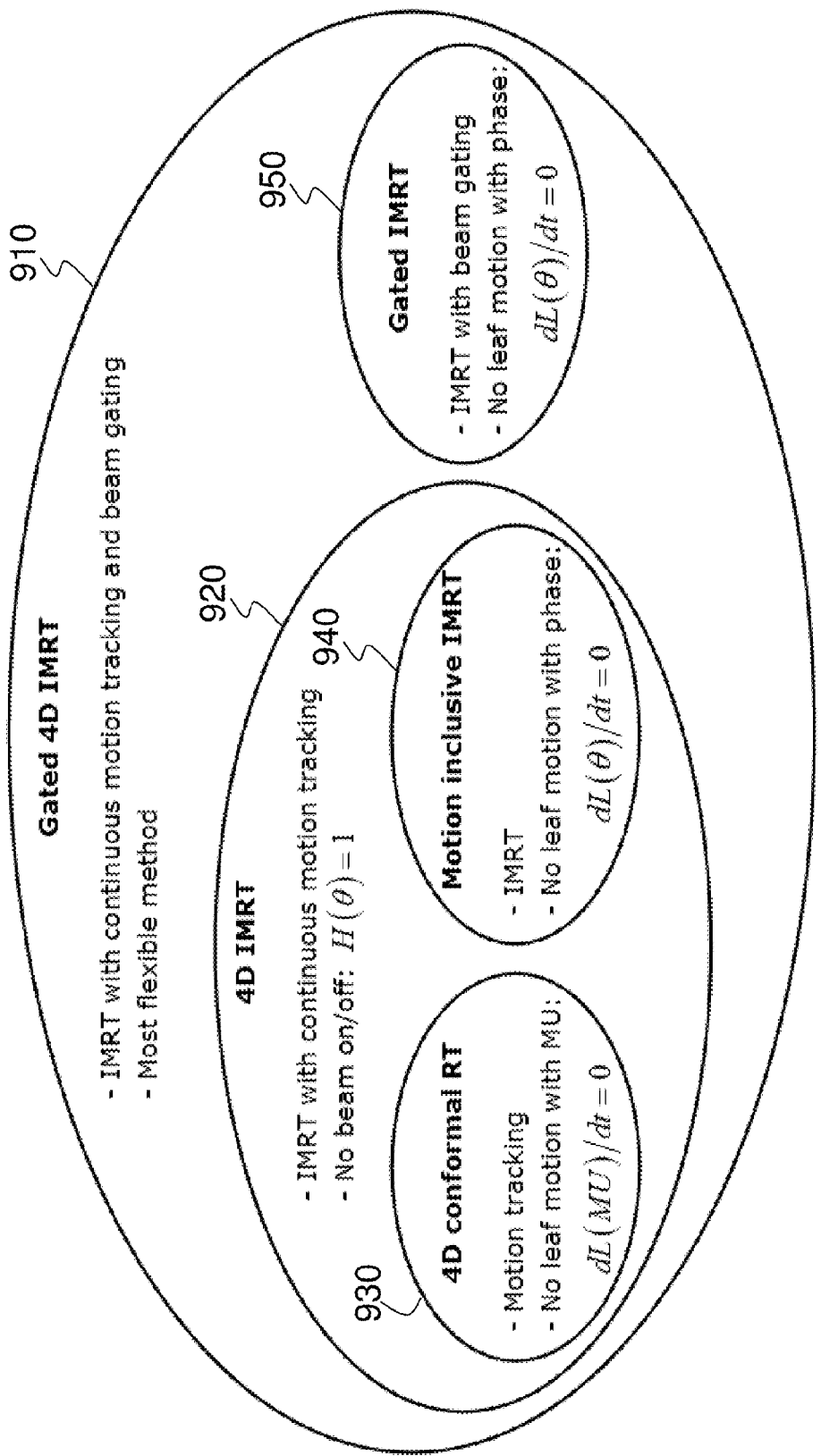
FIG. 9 is a schematic diagram showing the solution space and solution subspaces for a general framework for gated 4D IMRT treatments.

The general framework is to solve and investigate the contribution of the various degrees of freedom of a 4D planning optimization problem shown in FIG. 9, including (1) MLC leaf motion as a function of time (4D 920 vs. motion inclusive 940), (2) MLC leaf motion as a function of monitor unit (4D IMRT 920 vs. 4D conformal 930), and (3) beam on/off at different respiratory phases (gated 4D 910 vs. gated 950).

While 3D optimization of IMRT planning results in leaf sequence, L, as a function of monitor unit, MU, i.e., L(MU), optimizing IMRT planning for 4D anatomy adds an extra variable of the respiratory phase, θ, resulting in leaf sequence of L(MU,θ). A mathematical description of the 4D IMRT planning optimization is then to find the leaf sequence as a function of monitor unit and the respiratory phase, L(MU,θ), and beam on/off status, H(θ), to satisfy $$\min\{f[D(L(MU,\theta), H(\theta))]\}, \quad (2)$$

where the dose distribution to be delivered, D, is as follows:

$$D = \sum_{\theta=1}^{P} H(\theta)\lambda(\theta)d(I(\theta), I_{ref}, u(\theta), L(MU, \theta)) \quad (3)$$

with the nomenclature used shown in Table 4. To obtain the dose for a given respiratory phase, d, the dose is computed on I(θ) based on L(MU,θ) and then deformed to $I_{ref}$ using u(θ).

The main objective of the General Embodiment is to solve equation (2) for the five different scenarios shown in FIG. 9. The results of 4D IMRT planning using the five different scenarios will be compared using the existing 12 patient database and evaluated in terms of clinical and statistical significance. The variables to solve are L(MU,θ) and H(θ).

Compared to 3D IMRT optimization, the additional complexities are that:
1. the optimization is performed over many (P) image sets,
2. the MLC leaf motion is constrained by velocity constraints, $dL(MU,\theta)/dt \leq v_{max}$, where $v_{max}$ is the maximum leaf velocity, and
3. the patient respiratory signal during treatment is not known a priori due to the cycle-to-cycle and day-to-day variations in respiratory motion.

MLC Leaf Velocity Constraints

As MLC leaf acceleration, which has been measured to be ~50 cm sec$^{-2}$, is assumed to be sufficient for currently used dynamic leaf sequencing algorithm, only leaf velocity will be used as a constraint. For the current DMLC algorithms where leaf positions vary with monitor unit, leaf velocity is constrained to the maximum leaf velocity, $v_{max}$; i.e., $dL(MU)/dt \leq v_{max}$, where d(MU)/dt is the preplanned dose rate. For equation (2), $dL(MU,\theta)/dt \leq v_{max}$ is an additional complexity when the beam is on, i.e., when H(θ)=1.

It is important to note that this constraint is not just for motion along the leaf motion direction, but also motion perpendicular to the leaf motion direction, hence adjacent leaf ends should not be further apart than the maximum leaf velocity in a given phase transition. This constraint has been studied and is similar to synchronization to reduce MLC tongue and groove effects. The addition of the beam hold allows this constraint to be violated when the dosimetric penalty of the constraint is too high.

Given this complexity, the current practice to decouple dose calculations and leaf sequencing is undesirable because the planned doses may be quite different from the planned doses without constraints. Coupling dose calculations and leaf sequencing, though an additional computational burden, ensures that coupled plans are at least as good as decoupled plans. Also, so called "optimized" plans prior to leaf sequencing, which cannot be delivered, are not used for evaluation.

For the leaf i and control point j, leaf velocity constraint in terms of monitor unit is as follows:

$$L_{i,\theta,j} - L_{i,\theta,j-1} < v_{max} \cdot \Delta MU \cdot (t/MU), \quad (4)$$

where ΔMU is MU difference between control points of j−1 and j, and t is time in seconds. Leaf velocity constraint in terms of phase is divided into two different constraints, which are constraints for parallel and perpendicular to the target motion:

Parallel constraint: $L_{i,\theta} - L_{i,\theta-1} < v_{max} \cdot \lambda(\theta)$ Perpendicular constraint: $L_{i,\theta} - L_{i+1,\theta} < v_{max} \cdot \lambda(\theta)$ (5)

Note that violating these constraints occasionally is acceptable although it results in lower efficiency (longer treatment time), however it is better not to violate the constraints often.

SNOPT, Large-Scale Nonlinear Programming

The optimization method to determine L(MU,θ) and H(θ) is to use SNOPT, a general purpose system for constrained optimization, which is suitable for large-scale optimization problems (linear and nonlinear programs). SNOPT uses a sequential quadratic programming (SQP) algorithm that obtains search directions from a sequence of QP sub-problems.

Each QP sub-problem minimizes a quadratic model of a certain Lagrangian function subject to a linearization of the constraints. An augmented Lagrangian merit function is reduced along each search direction to ensure convergence from any starting point.

Methods to Solve

Steps to solve 4D IMRT optimization problem are as follows:

Step 1: Initialization
For each respiratory phase, set beam is on, i.e., H(θ)=1 ∀ θ, and L(MU,θ) such that the radiation field aperture defines planning target volume (PTV) plus a margin for penumbra.

Step 2: Updating
Calculate D using equation (2).
Calculate f using equation (1).

Step 3: Iteration (to Minimize f)
Determine $$\frac{\partial f}{\partial H}.$$

Boundary condition for H is to keep the minimum of four phases for treatment efficiency; i.e., the minimum of ΣH(θ)=4.

Determine whether beam is on or not for a given phase, θ, calculate $D_\theta$, which is D without the phase θ, and compute f from D (averaged over all 10 phases) and from $D_\theta$ (averaged over 9 phases without the phase θ). Then, compare the two f values and determine to keep the phase or not.

For example, calculate $$D = \frac{\sum_{\theta=1}^{10} D(\theta)}{10}$$

and D without θ=1, $$D_1 = \frac{\sum_{\theta=2}^{10} D(\theta)}{9},$$

and compute two $f$s.

If $f$ from $D_1$ is smaller than that from D, keep the phase 1. Repeat this for all 10 phases, and find only good phases, keeping at least four phases for efficiency. Determine $$\frac{\partial f}{\partial L}.$$

Update $L(MU,\theta)$ including leaf motion constraints.

Iterates k times until $f_k - f_{k-1} < \delta$, where $\delta$ is a convergence threshold, and return to Step 2.

Tables

Tables used in the above Specific Embodiment and General Embodiment will now be stated:

TABLE 1

Patient gross tumor volume (GTV), GTV centroid motion range, and motion range in major axis

| Patient no. | GTV volume (cm³) | GTV centroid motion (cm) | Motion in major axis (cm) |
|---|---|---|---|
| 1 | 3.0 | 2.1 | 1.6 |
| 2 | 61.0 | 0.4 | 0.4 |
| 3 | 12.5 | 0.5 | 0.5 |
| 4 | 1.0 | 0.6 | 0.6 |
| 5 | 20.4 | 0.1 | 0.1 |
| 6 | 5.2 | 0.4 | 0.4 |
| 7 | 323.6 | 0.2 | 0.2 |
| 8 | 23.0 | 0.3 | 0.2 |
| 9 | 6.1 | 0.2 | 0.2 |
| 10 | 7.5 | 0.5 | 0.4 |
| 11 | 119.2 | 1.3 | 1.1 |
| 12 | 7.5 | 1.1 | 0.9 |
| Mean (minimum, maximum) | 49.2 (1.0, 323.6) | 0.7 (0.1, 2.1) | 0.6 (0.1, 1.6) |

TABLE 2

A comparison of the dose-volume metrics of individual phase plans using the deliverable and three-dimensional (3D) optimal methods

| | PTV | | Lungs-GTV | | Spinal cord |
|---|---|---|---|---|---|
| | $(D_{mean})_{opt}^{del}$ | $(D_{95\%})_{opt}^{del}$ | $(D_{mean})_{opt}^{del}$ | $(V_{20})_{opt}^{del}$ | $(D_{0.1\%})_{opt}^{del}$ |
| Mean ± SD | 1.001 ± 0.004 | 0.992 ± 0.016 | 1.00 ± 0.02 | 1.01 ± 0.03 | 1.00 ± 0.05 |
| Minimum, Maximum | 0.988, 1.021 | 0.916, 1.010 | 0.93, 1.05 | 0.90, 1.12 | 0.88, 1.31 |
| p | 0.11 | 0.09 | 0.48 | 0.46 | 0.48 |
| | Esophagus | | Heart | | Thorax-PTV |
| | $(D_{mean})_{opt}^{del}$ | $(V_{55})_{opt}^{del}$ | $(D_{mean})_{opt}^{del}$ | $(V_{40})_{opt}^{del}$ | $(D_{mean})_{opt}^{del}$ |
| Mean ± SD | 1.00 ± 0.03 | 1.02 ± 0.07 | 1.01 ± 0.05 | 0.96 ± 0.20 | 1.00 ± 0.02 |
| Min, max | 0.88, 1.10 | 0.96, 1.56 | 0.87, 1.26 | 0.00, 1.17 | 0.93, 1.03 |
| p | 0.50 | 0.44 | 0.49 | 0.45 | 0.50 |

Mean and SD of the dose-volume metric ratios averaged over all 10 phases for all 12 patients; and p values testing whether two distributions are statistically different. $D_{mean}$ represents the dose received by mean volume of the PTV or organs at risk (OARs); $D_{A\%}$ the dose received by A % of volume of the PTV or OARs; and $V_B$ the total volume of OARs receiving at least B Gy.

TABLE 3

A comparison of the dose-volume metrics of four-dimensional (4D) plans using the deliverable and three-dimensional (3D) optimal methods

| | PTV | | Lungs-GTV | | Spinal cord |
|---|---|---|---|---|---|
| | $(D_{mean})_{opt}^{del}$ | $(D_{95\%})_{opt}^{del}$ | $(D_{mean})_{opt}^{del}$ | $(V_{20})_{opt}^{del}$ | $(D_{0.1\%})_{opt}^{del}$ |
| Mean ± SD | 1.001 ± 0.002 | 0.995 ± 0.009 | 1.00 ± 0.02 | 1.01 ± 0.03 | 1.00 ± 0.02 |
| Minimum, maximum | 0.999, 1.007 | 0.974, 1.009 | 0.97, 1.03 | 0.97, 1.08 | 0.96, 1.04 |
| p | 0.32 | 0.39 | 0.49 | 0.49 | 0.50 |

TABLE 3-continued

A comparison of the dose-volume metrics of four-dimensional (4D) plans using the deliverable and three-dimensional (3D) optimal methods

| | Esophagus | | Heart | | Thorax-PTV |
| --- | --- | --- | --- | --- | --- |
| | $(D_{mean})_{opt}^{del}$ | $(V_{55})_{opt}^{del}$ | $(D_{mean})_{opt}^{del}$ | $(V_{40})_{opt}^{del}$ | $(D_{mean})_{opt}^{del}$ |
| Mean ± SD | 1.00 ± 0.02 | 1.02 ± 0.05 | 1.01 ± 0.03 | 1.00 ± 0.10 | 1.00 ± 0.01 |
| Min, max | 0.96, 1.03 | 0.97, 1.11 | 0.95, 1.05 | 0.77, 1.20 | 0.97, 1.02 |
| p | 0.50 | 0.48 | 0.50 | 0.49 | 0.50 |

Mean and SD of the dose-volume metric ratios averaged over all 12 patients; and p values testing whether two distributions are statistically different. $D_{mean}$ represents the dose received by mean volume of the PTV or organs at risk (OARs); $D_{A\%}$ the dose received by A % of volume of the PTV or OARs; and $V_B$ the total volume of OARs receiving at least B Gy.

TABLE 4

The variables, description, and typical range and sizes.

| Variable | Description | Type/range/size |
| --- | --- | --- |
| f | Mathematical cost function representation of a clinical objective | Function of arbitrary form evaluating dose in segmented anatomy, typically dose, dose-volume, or estimated outcome based |
| D | Summed 4D dose distribution | 3D density distribution of typically $10^6$ voxels |
| θ | Respiratory phase index from 1 to the maximum number of phases, P | Discrete index of typical size 10 |
| H | Heavyside function where a H(θ) = 0 corresponds to beam off and a H(θ) = 1 beam on | Binary for each respiratory phase |
| λ | Time spent per each phase normalized such that $$\sum_{\theta=1}^{P} H(\theta)\lambda(\theta) = 1$$ | Continuous variable of typical size 10 |
| d | Dose for a given respiratory phase computed on 3D CT image, I, given leaf sequence, L, (superposition algorithm to be used in this study) deformed to a given source phase, $I_{ref}$ | 3D density distribution of typically $10^6$ voxels |
| I | 4D CT image of anatomy, where I(θ) represents a given 3D instance for a respiratory phase and $I_{ref}$ corresponds to the image used for dose summation | 4D density distribution of typically $10^7$ voxels at 10 time points |
| u | Displacement vector field computed using deformable registration mapping images from a given respiratory phase, θ, to the reference phase | 3D vector field of typically $10^7$ vectors |
| L | Position of each MLC leaf tip for each field planned which can change with MU for each field and θ. Due to mechanical constraints, leaf motion is limited by the maximum leaf velocity, i.e., $dL/dt \leq v_{max}$. | Continuous variable for each field (5-9) for each leaf (80-160), for each MU control point (5-400) for each respiratory phase (10) |

CONCLUSIONS

In the above described Specific Embodiment a deliverable 4D IMRT planning method was developed and applied to 12 patient 4D CT image sets. This method yields similar dose distributions for each of the individual phase plans and statistically equivalent dosimetric values compared with the 3D optimal method, indicating the deliverable method is dosimetrically robust to the variations of fractional time spent in respiratory phases on a given 4D CT scan. Nonlinear target motion and deformation do not cause significant dose discrepancies. The deliverable 4D IMRT planning method according to the above described specific embodiment has a clear path to clinical implementation.

The above described General Embodiment provides an implementation of the invention that also serves as a framework for testing the hypothesis that using respiratory motion as an additional degree of freedom will result in significantly improved IMRT plans.

While the invention has been described in terms of preferred embodiments, those skilled in the art will recognize that the invention can be practiced with modification within the spirit and scope of the appended claims.

The invention claimed is:

1. A method for four-dimensional (4D) intensity modulated radiation therapy (IMRT) planning for motion compensated treatments, comprising:
   creating a deliverable IMRT treatment plan for a tumor in irregular periodic motion, said irregular period of motion comprising a plurality of phases, said treatment plan comprising treatment plans for each of said plurality of phases, each said treatment plan being delivered using a multi-leaf collimator, leaf positions of said multi-leaf collimator being adapted separately for each respective phase and for each of a plurality of beam positions, the beam being collimated by said multi-leaf collimator,
   determining a gross tumor volume (GTV) centroid for each of said plurality of phases;
   designating one of said plurality of phases as a reference phase; and
   targeting said collimator for each phase by a displacement relative to the GTV centroid of the reference phase,
   wherein said phases are defined by dividing said irregular period into equal parts of time, wherein said adapted leaf positions are constant during each phase, and wherein a collimator angle for each said beam position is aligned to a major axis of motion of the GTV centroid over said plurality of phases as viewed by said beam (BEV).

2. A method as in claim 1, wherein each IMRT treatment plan for a phase is generated by translating leaf positions by the displacement of the GTV centroid for each phase relative to the reference phase, keeping the collimator angle for each beam the same.

3. A for four-dimensional (4D) intensity modulated radiation therapy (IMRT) planning for motion compensated treatments, comprising:
   means for creating a deliverable IMRT treatment plan for a tumor in irregular periodic motion, said irregular period of motion comprising a plurality of phases, said treatment plan comprising treatment plans for each of said plurality of phases;
   a multi-leaf collimator for delivering each said treatment plan, the leaf positions of said multi-leaf collimator being adapted separately for each respective phase and for each of a plurality of beam positions, the beam being collimated by said multi-leaf collimator,
   means for determining a gross tumor volume (GTV) centroid for each of said plurality of phases;
   means for designating one of said plurality of phases as a reference phase; and
   means for targeting said collimator for each phase by a displacement relative to the GTV centroid of the reference phase,
   wherein said phases are defined by offsets from said reference phase, said offsets being measured by time or position within said irregular period,
   wherein said adapted leaf positions are constant during each phase, and
   wherein a collimator angle for each said beam position is aligned to a major axis of motion of the GTV centroid over said plurality of phases as viewed by said beam (BEV).

4. A system as in claim 3, wherein each IMRT treatment plan for a phase is generated by translating leaf positions by the displacement of the GTV centroid for each phase relative to the reference phase, keeping the collimator angle for each beam the same.

* * * * *